(12) United States Patent
Bierman et al.

(10) Patent No.: US 8,684,976 B2
(45) Date of Patent: *Apr. 1, 2014

(54) UNIVERSAL CATHETER ANCHORING SYSTEM

(75) Inventors: Steven F. Bierman, Del Mar, CA (US); Wayne T. Mitchell, Cardiff, CA (US); Richard A. Pluth, San Diego, CA (US)

(73) Assignee: Venetec International, Inc., Covington, GA (US)

( * ) Notice: Subject to any disclaimer, the term of this patent is extended or adjusted under 35 U.S.C. 154(b) by 234 days.

This patent is subject to a terminal disclaimer.

(21) Appl. No.: 13/193,519

(22) Filed: Jul. 28, 2011

(65) Prior Publication Data

US 2011/0288489 A1   Nov. 24, 2011

Related U.S. Application Data

(63) Continuation of application No. 13/115,013, filed on May 24, 2011, now Pat. No. 8,298,191, which is a continuation of application No. 11/837,447, filed on Aug. 10, 2007, now Pat. No. 7,955,307, which is a continuation of application No. 10/909,469, filed on Aug. 2, 2004, now Pat. No. 7,837,655, which is a continuation of application No. 09/897,717, filed on Jun. 29, 2001, now Pat. No. 6,770,055, which is a continuation-in-part of application No. 09/513,054, filed on Feb. 24, 2000, now Pat. No. 6,582,403.

(60) Provisional application No. 60/215,100, filed on Jun. 29, 2000.

(51) Int. Cl.
*A61M 5/32* (2006.01)

(52) U.S. Cl.
USPC ........... 604/174; 604/175; 604/176; 604/177; 604/178; 604/179; 604/180

(58) Field of Classification Search
USPC ................................... 604/174–180
See application file for complete search history.

(56) References Cited

U.S. PATENT DOCUMENTS

| | | | |
|---|---|---|---|
| 3,167,072 A | 1/1965 | Stone et al. | |
| 3,834,380 A | 9/1974 | Boyd | |

(Continued)

FOREIGN PATENT DOCUMENTS

| | | |
|---|---|---|
| GB | 2 086 466 | 5/1982 |
| JP | 63-211700 | 9/1988 |

(Continued)

*Primary Examiner* — Bhisma Mehta
*Assistant Examiner* — Larry R Wilson
(74) *Attorney, Agent, or Firm* — Knobbe Martens Olson & Bear, LLP

(57) ABSTRACT

A method of securing a medical article to the body of a patient is disclosed in which an anchoring device comprising an anchor and a retainer is used. The retainer is attached to an upper surface of the anchor and comprises a base, a cover and a post. The base is disposed on the upper surface of the anchor and the cover is connected to the base so as to move between an open and a closed position. When the cover is in the closed position, it lies above at least part of the base. The post is attached movably to either the base or the cover and is arranged so as to lie at least partially between the cover and the base when the cover is in the closed position. When securing a medical article, the cover is placed in the open position and the medical article placed onto the retainer. The cover may then be closed over the medical article and the anchoring device attached to the patient.

20 Claims, 18 Drawing Sheets

(56) References Cited

U.S. PATENT DOCUMENTS

| | | |
|---|---|---|
| 4,114,618 A | 9/1978 | Vargas |
| 4,129,128 A | 12/1978 | McFarlane |
| 4,161,177 A | 7/1979 | Fuchs |
| 4,193,174 A | 3/1980 | Stephens |
| 4,224,937 A | 9/1980 | Gordon |
| 4,248,229 A | 2/1981 | Miller |
| 4,250,880 A | 2/1981 | Gordon |
| 4,333,468 A | 6/1982 | Geist |
| 4,362,156 A | 12/1982 | Feller, Jr. et al. |
| 4,397,647 A | 8/1983 | Gordon |
| 4,449,975 A | 5/1984 | Perry |
| 4,453,933 A | 6/1984 | Speaker |
| 4,517,971 A | 5/1985 | Sorbonne |
| 4,645,492 A | 2/1987 | Weeks |
| 4,742,824 A | 5/1988 | Payton et al. |
| 4,808,162 A | 2/1989 | Oliver |
| 4,857,058 A | 8/1989 | Payton |
| 4,863,432 A | 9/1989 | Kvalo |
| 4,897,082 A | 1/1990 | Erskine |
| 4,898,587 A | 2/1990 | Mera |
| 4,919,654 A | 4/1990 | Kalt |
| 4,976,700 A | 12/1990 | Tollini |
| 4,997,421 A | 3/1991 | Palsrok et al. |
| 5,037,397 A | 8/1991 | Kalt et al. |
| 5,037,398 A | 8/1991 | Buchanan |
| 5,084,026 A | 1/1992 | Shapiro |
| 5,098,399 A | 3/1992 | Tollini |
| 5,137,519 A | 8/1992 | Littrell et al. |
| 5,192,273 A | 3/1993 | Bierman et al. |
| 5,192,274 A | 3/1993 | Bierman |
| 5,232,453 A | 8/1993 | Plass et al. |
| 5,266,401 A | 11/1993 | Tollini |
| 5,342,317 A | 8/1994 | Claywell |
| 5,354,282 A | 10/1994 | Bierman |
| 5,382,239 A | 1/1995 | Orr et al. |
| 5,456,671 A | 10/1995 | Bierman |
| 5,496,283 A | 3/1996 | Alexander |
| 5,549,567 A | 8/1996 | Wolman |
| D375,355 S | 11/1996 | Bierman |
| 5,637,098 A | 6/1997 | Bierman |
| 5,638,814 A | 6/1997 | Byrd |
| 5,681,290 A | 10/1997 | Alexander |
| 5,693,032 A | 12/1997 | Bierman |
| 5,702,371 A | 12/1997 | Bierman |
| D389,911 S | 1/1998 | Bierman |
| 5,722,959 A | 3/1998 | Bierman |
| 5,782,807 A | 7/1998 | Falvai et al. |
| 5,792,115 A | 8/1998 | Horn |
| 5,795,335 A | 8/1998 | Zinreich |
| 5,800,402 A | 9/1998 | Bierman |
| D399,954 S | 10/1998 | Bierman |
| 5,827,239 A | 10/1998 | Dillon et al. |
| 5,855,591 A | 1/1999 | Bierman |
| 5,871,189 A | 2/1999 | Hoftman |
| 6,117,163 A | 9/2000 | Bierman |
| 6,132,398 A | 10/2000 | Bierman |
| 6,213,979 B1 * | 4/2001 | Bierman .................. 604/174 |
| 6,231,548 B1 | 5/2001 | Bassett |
| 6,283,945 B1 | 9/2001 | Bierman |
| 6,343,616 B1 | 2/2002 | Houtchens |
| 6,361,523 B1 | 3/2002 | Bierman |
| 6,491,664 B2 | 12/2002 | Bierman |
| 6,572,588 B1 | 6/2003 | Bierman et al. |
| 7,955,307 B2 * | 6/2011 | Bierman et al. .............. 604/180 |
| 8,298,191 B2 * | 10/2012 | Bierman et al. .............. 604/180 |

FOREIGN PATENT DOCUMENTS

| | | |
|---|---|---|
| WO | WO 94/12231 | 6/1994 |
| WO | WO 96/10435 | 4/1996 |
| WO | WO 98/53872 | 12/1998 |
| WO | WO 99/20334 | 4/1999 |
| WO | WO/99 25399 | 5/1999 |

* cited by examiner

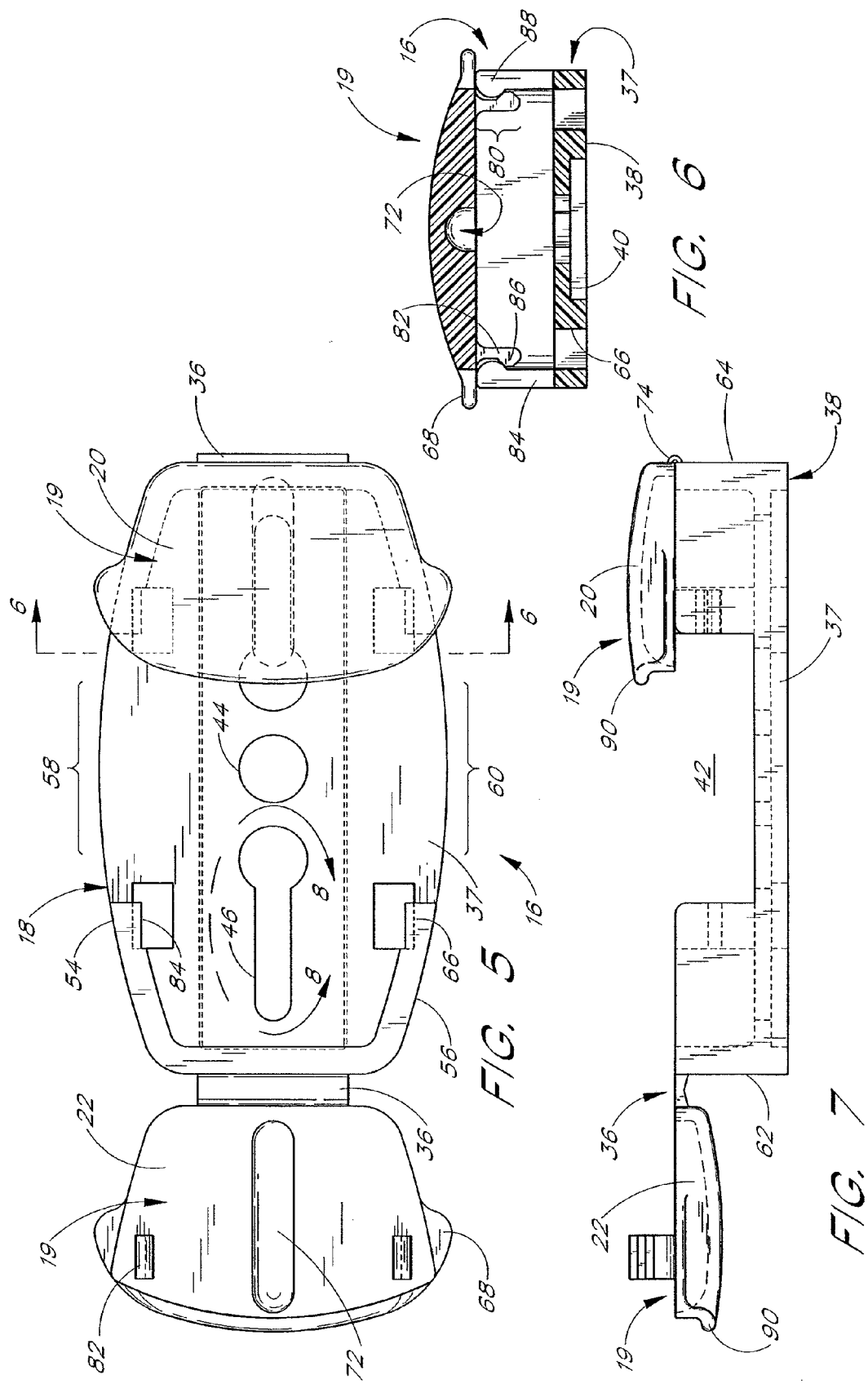

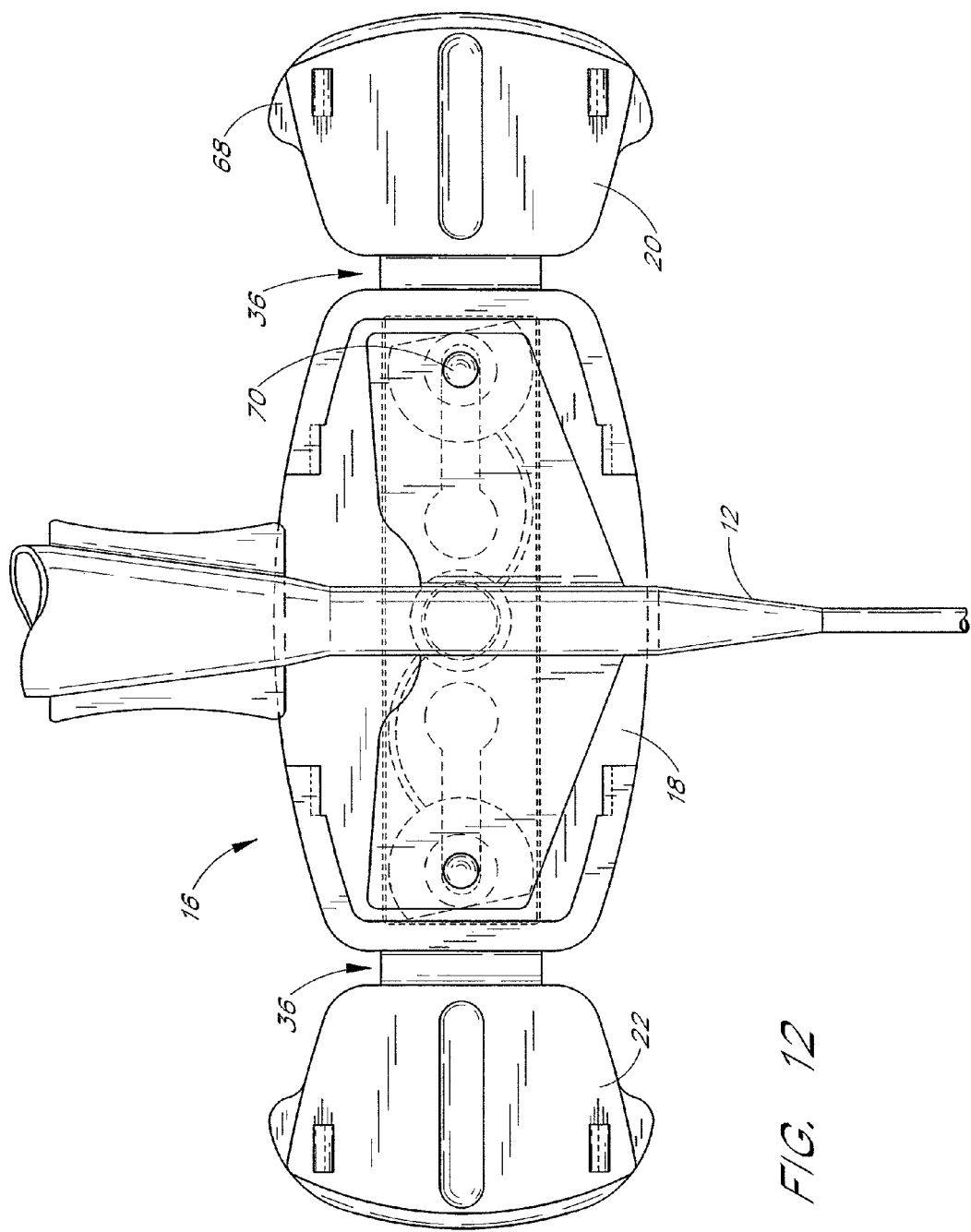

UNIVERSAL CATHETER ANCHORING SYSTEM

RELATED CASES

This application is a continuation of U.S. patent application Ser. No. 13/115,013 filed on May 24, 2011, which is a continuation of U.S. patent application Ser. No. 11/837,447 filed on Aug. 10, 2007, now issued as U.S. Pat. No. 7,955,307 on Jun. 7, 2011, which is a continuation of U.S. patent application Ser. No. 10/909,469 filed on Aug. 2, 2004, now issued as U.S. Pat. No. 7,837,655 on Nov. 23, 2010, which is a continuation of U.S. patent application Ser. No. 09/897,717 filed on Jun. 29, 2001, now issued as U.S. Pat. No. 6,770,055 on Aug. 3, 2004, which is a continuation-in-part of U.S. patent application Ser. No. 09/513,054 filed on Feb. 24, 2000, now issued as U.S. Pat. No. 6,582,403 on Jun. 24, 2003 and also claims priority under 35 U.S.C. §119(e) from Provisional Application No. 60/215,100 filed on Jun. 29, 2000, all of which are hereby expressly incorporated by reference in their entireties.

BACKGROUND OF THE INVENTION

1. Field of the Invention

The present invention relates in general to a universal anchoring system for securing a medical article to a patient and, in particular, to a universal anchoring system for securing a catheter to a patient to inhibit movement or migration of the catheter relative to the patient.

2. Description of Related Art

It is common in the treatment of patients to utilize catheters to introduce fluids and medications directly into the patient or to withdraw fluids from the patient. An example of a typical catheter is a central venous catheter, or CVC, which is used to introduce fluids through a central vein.

In most cases, the catheter remains in place for many days. In order to secure the catheter in position at the insertion site, a healthcare worker often secures the catheter to the patient using tape. That is, the healthcare worker commonly places long pieces of tape across the portion of the catheter near the insertion site in a crisscross pattern to secure the catheter to the patient's skin. This securement inhibits disconnection between the catheter and the insertion site, and also prevents the catheter from snagging on the bed rail or other objects.

Tape, however, often collects dirt and other contaminates. Normal protocol therefore requires periodic (e.g., daily) tape changes to inhibit bacteria and germ growth at the securement site. These frequent tape changes often excoriate the patient's skin. Additionally, valuable time is spent by healthcare workers applying and reapplying the tape. Because many healthcare workers find the taping procedure cumbersome and difficult to accomplish when wearing gloves, they often remove their gloves when taping. Not only does this increase the amount of time spent on the taping procedure, but it also subjects the healthcare worker to an increased risk of infection. Moreover, even if healthcare workers remain gloved, contact between the adhesive surface of the tape and the latex gloves can cause micro-holes in the gloves, subjecting the healthcare worker to possible infection.

A variety of catheter securement devices have been developed to obviate the need for frequent application of tape to secure a catheter to a patient. One such securement device provides a flexible clamp with winged extensions that are sutured to the patient's skin. In some applications, the winged extensions are integrally formed with catheter. In other applications, the flexible clamp is covered by a rigid fitting, which receives the catheter/clamp combination in a friction-fit manner. The rigid fitting and flexible clamp are formed with lateral, aligned holes, which allow the combination to be sutured to the patient's skin. Although these suturing devices securely attach the catheter to the patient, it is obviously painful and uncomfortable for the patient. These devices are also time consuming and inconvenient to secure, pose the risk of needle-stick to the health care provider, and risk suture-site infection to the patient.

In addition, suture material tends to exhibit poor gripping on medical tubes and can cut through the winged extension of the flexible clamp if a rigid clamp is not used. However, the use of a rigid fitting complicates the securement procedure by adding yet another component that can be dropped on the floor and become unsterile. In addition, the sutured securement of the flexible clamp and/or the rigid fitting assembly does not permit easy release of the catheter from the patient for dressing changes and insertion site cleaning. A removal instrument (e.g., sterile scissors) also is generally required for suture removal.

Rather than suturing lateral, aligned holes to a patient's skin, other catheter securement devices provide an adhesive layer or resilient band interposed between the flexible clamp and the patient's skin. See, for example, U.S. Pat. Nos. 5,342,317; 5,192,274; 5,084,026; 4,449,975; and 4,250,880. Many of these securement devices, however, suffer from one or more of the following disadvantages: are time consuming and inconvenient to secure; have multiple parts, which can be dropped and become none sterile; and require removal instruments (e.g., hemostat or scissors) to disengage the catheter from the securement device.

Additionally, no standard exists regarding spacing of the lateral holes of the catheters and catheter fittings. Manufacturers invariably produce catheters and catheter fittings with holes having varying geometries and distances therebetween. Prior securement devices thus become dedicated to fit and secure only certain catheters.

SUMMARY OF THE INVENTION

The present invention provides a simply-structured anchoring system that secures a catheter in a fixed position, but easily releases the catheter for dressing changes or other servicing. The present invention also recognizes that prior art catheter anchoring systems have been dedicated to a particular catheter, catheter fitting or catheter manufacturer. Thus, the present anchoring system also can cooperate with the suture or mounting holes of many different catheter and catheter fitting designs. In particular, the present anchoring system can be adjusted so as to be used with a variety of catheters and/or catheter fittings which have varying distances between the suture or mounting holes of the catheter and/or fitting. The present invention also provides a technique for anchoring medical articles to a patient in a fixed position and allowing for the release of those articles.

One aspect of the present invention involves an anchoring system for securing a medical article to the body of a patient. The anchoring system comprises an anchor pad having an upper surface and a lower surface. At least a portion of the lower surface has an adhesive surface to attach the anchor pad to the body of the patient. A retainer is mounted on the upper surface of the anchor pad and is capable of receiving a portion of the medical article. The retainer includes a base, a cover, and a post. The base is disposed on the upper surface of the anchor pad and the cover is movable connected to the base so as to move between an open position and a closed position. The cover lies above at least part of the base when in the closed position. The post is movably coupled to one of the base and the cover and is arranged on the retainer so as to at least partially lie between the cover and the base when the cover is in the closed position.

In accordance with another aspect of the present invention, an anchoring system is provided for securing a medical article to the body of a patient. The anchoring system comprises an anchor pad having an upper surface and a lower surface. At least a portion of the lower surface has an adhesive surface to attach the anchor pad to the body of the patient. A retainer is mounted on the upper surface of the anchor pad and is capable of receiving a portion of the medical article. The retainer includes a base, a post, and a cover assembly. The cover assembly includes including at least two covers, each cover being connected to the base by a hinge mechanism. Each cover being movable between at least two positions: an open position and a closed position. The post is coupled to one of the base and covers and is arranged on the retainer so as to at least partially lie between the base and at least one of the covers when the cover is in the closed position.

One aspect of the present invention accordingly involves an anchoring system for securing a medical article to the body of a patient. The anchoring system comprises an anchor pad, a retainer, and a post subassembly. The retainer is mounted on the upper surface of the anchor pad and includes a base, a cover assembly, and a latching mechanism. The base receives the medical article to be secured, and the cover assembly can be moved between an open and a closed position. In the open position, the medical article can be inserted or removed from the retainer. In the closed position, a channel is formed within which the medical article is held securely. The latching mechanism operates between the base and the cover assembly to hold it in the closed position. The post subassembly includes a number of posts that protrude into the channel of the retainer and interact with the medical article to prevent any inadvertent motion.

In one preferred mode, the post subassembly includes posts that are movable with respect to the base of the retainer and to each other, so as to accommodate mounting or suture hole spacings of various distances. In another mode, the post subassembly includes posts that are fixed relative to the base.

In a preferred mode, the cover assembly of the retainer is divided into two separate covers which are independently latched to the base and which can independently be adjusted between the open and closed positions.

In accordance with each of the aspects of the invention summarized above, the anchoring system can also include a fitting. The fitting can be part of the medical line itself or can be a separate component that can be attached to the medical line. For example, in one mode, the medical article can be a catheter with an integral fitting. The fitting can also be a removable fitting (e.g., a movable wing clamp) that is releasably attached to the catheter. As such, these components can comprise an anchoring system kit, where one or more sizes of fittings are included in the kit in order to accommodate catheters of differing sizes.

In accordance with another aspect of the invention, a method for anchoring a medical article using an anchoring device is presented. The anchoring device has an anchor and a retainer. The retainer has a base and at least one cover. A post is disposed either upon the base or the cover and when the cover is moved into a closed position, the post lies at least partially between the cover and the base. When securing a medical article, the cover is placed in an open position, a portion of a medical article is placed within the base, and then the cover is closed to engage the retainer with the medical article and the anchoring device may then be secured to the patient.

In accordance with a further aspect of the method, the anchor may be an anchor pad with an adhesive surface which is attached to the skin of a patient and upon which the retainer is mounted.

In accordance with another further aspect of the method, a second post may be provided on the retainer of the anchoring device.

In another further aspect of the method, a second cover may be provided on the anchoring device.

In accordance with another aspect of the method described above, a lower support member may be provided which lies between the base of the retainer of the anchoring device and the anchor.

In a further aspect of the method, the lower support member may be formed unitarily with the base of the retainer.

Further aspects, features and advantages of the present invention will become apparent from the detailed description of the preferred embodiments that follow.

BRIEF DESCRIPTION OF THE DRAWINGS

The above mentioned and other features of the invention will now be described with reference to the drawings of a preferred embodiment of the present anchoring system. The illustrated embodiment of the anchoring system is intended to illustrate, but not to limit the invention. The drawings contain the following figures:

FIG. 5 is a top plan view of the base and covers of the retainer of FIG. 1 shown with one cover in the open position and one cover in the closed position;

FIG. 6 is a cross sectional side view of the retainer of FIG. 5 taken along line 6-6;

FIG. 7 is a front elevational view of the retainer of FIG. 5;

FIG. 12 is a top plan view of the assembled retainer of FIG. 1, including the base, covers and post platform, shown with an exemplary catheter in the channel of the retainer and the covers in the open position;

DETAILED DESCRIPTION OF THE PREFERRED EMBODIMENTS

Figure 3:
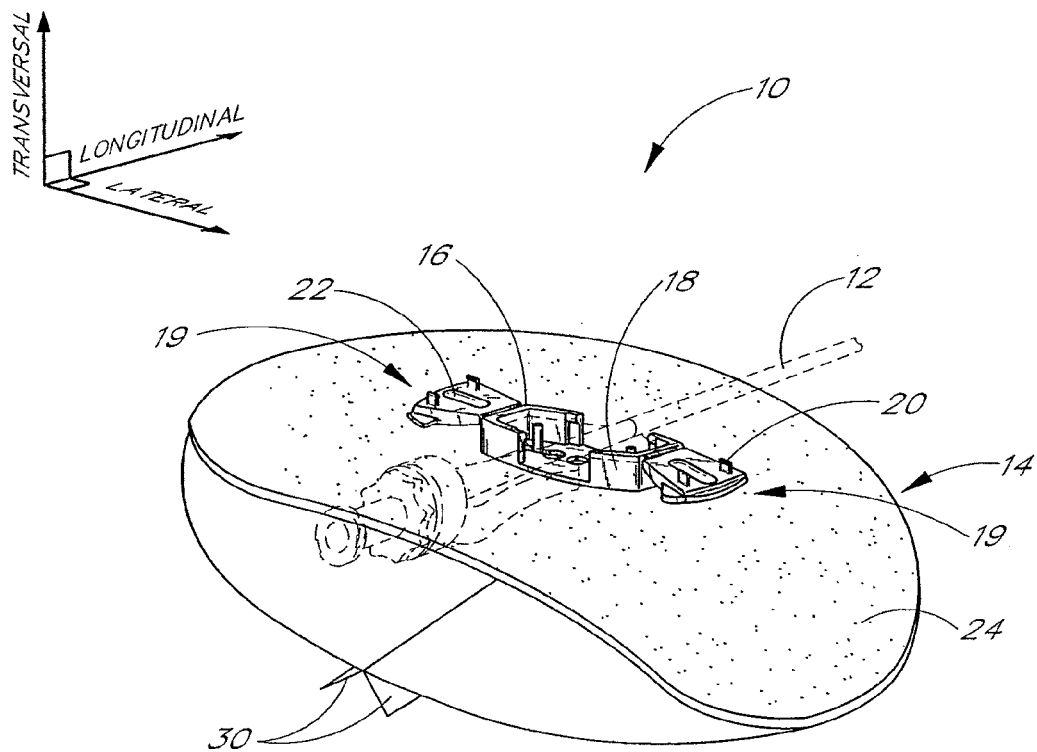
FIG. 3 is a perspective view of the anchoring system of FIG. 1 illustrated with the covers in the open position and an exemplary catheter illustrated by phantom lines in an inserted position within the retainer.

The present embodiment of the catheter anchoring system, which is generally designated by reference numeral 10, is disclosed in the context of use with an exemplary CVC (as shown in FIG. 3 and designated by reference numeral 12).

The principles of the present invention, however, are not limited to catheters. Instead, it will be understood by one of ordinary skill in this art, in view of the present disclosure, that the anchoring system and/or retainer disclosed herein also can be successfully utilized in connection with other types of medical articles, including, but not limited to, other types of catheters, fluid drainage and delivery tubes and electrical wires. For example, but without limitation, the retainer disclosed herein also can be configured to receive and secure peripheral catheters, peripherally inserted central catheters, hemodialysis catheters, surgical drainage tubes, feeding tubes, chest tubes, nasogastric tubes, scopes, as well as electrical wires or cables connected to external or implanted electronic devices or sensors. One skilled in the art may also find additional applications for the devices and systems disclosed herein. Thus, the illustration and description of the anchoring system in connection with a CVC is merely exemplary of one possible application of the anchoring system.

Each of the embodiments described herein employs some basic concepts characteristic of the present anchoring system, namely releasable engagement of the catheter to the patient. The releasable engagement is achieved by cooperation among a base, at least one cover and at least one post element. This cooperation allows the catheter to be disconnected from the anchoring system and from the patient, for any of a variety of known purposes. For instance, the healthcare worker may want to remove the catheter from the anchoring system to ease disconnection of the catheter from the insertion point or to clean the patient. The disengagement of the catheter from the anchoring system, however, can be accomplished without removing the anchoring system from the patient.

Common to each the described embodiments, the present anchoring system inhibits axial movement of the catheter with respect to the anchoring system, and hence, with respect to the insertion site on the patient. Transverse and lateral movement is generally arrested by the holding effect provided by the base and cover assembly, as well as by the cooperative interaction between at least one post member and an opening on the catheter and/or catheter fitting. That is, the base and cover assembly surround the catheter while the post(s) extends through a corresponding suture or mount opening(s) formed on the catheter and/or catheter fitting. Longitudinal movement is similarly arrested by the interaction between the post(s) and the opening(s).

In one form, the present anchoring system also is adapted to receive at least several different types or styles of catheters and/or catheter fittings. In particular, the spacing between the posts and/or the spacing between a post and either the cover assembly or base can be varied in order to accommodate catheters and/or catheter fittings with differing spacings between the suture holes. This feature can also be used to accommodate catheters and/or catheter fittings having different sizes and/or shapes. In one of the embodiments described below, the retainer includes two posts, each of which is movable with respect to the other and also with respect to the cover assembly and the base of the retainer. In another embodiment, one of the posts is fixed and the other is movable. The spacing between the posts, as well as the spacing between the movable post and the adjacent base/cover structure, can be varied by moving the one post. In other variations, the post(s) can be fixed to a cover or base section which can move relative to another section of the retainer to changes the position of the post(s) on the retainer. So configured, the lateral width between posts can be adjusted to receive and secure a variety of catheters and/or catheter fittings. Various other aspects of the present invention, however, can be used apart from this "universal" feature, as will be apparent from the discussion of the embodiments below.

To assist in the description of these components of the anchoring system 10 (see FIG. 3), the following coordinate terms are used. A "longitudinal axis" is generally parallel to the section of the catheter 12 retained by the anchoring system 10. A "lateral axis" is normal to the longitudinal axis and is generally parallel to the plane of the anchor pad 14. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. Also, the terms "proximal" and "distal," which are used to describe the present anchoring system 10, are used consistently with the description of the exemplary applications. Thus, proximal and distal are used in reference to the center of the patient's body. The terms "upper," "lower," "top," "bottom," and the like, which also are used to describe the present anchoring system 10, are used in reference to the illustrations of the embodiments. A detailed description of the anchoring system 10, and its associated method of use, now follows.

Dual Cover Retainer System

Figure 1:
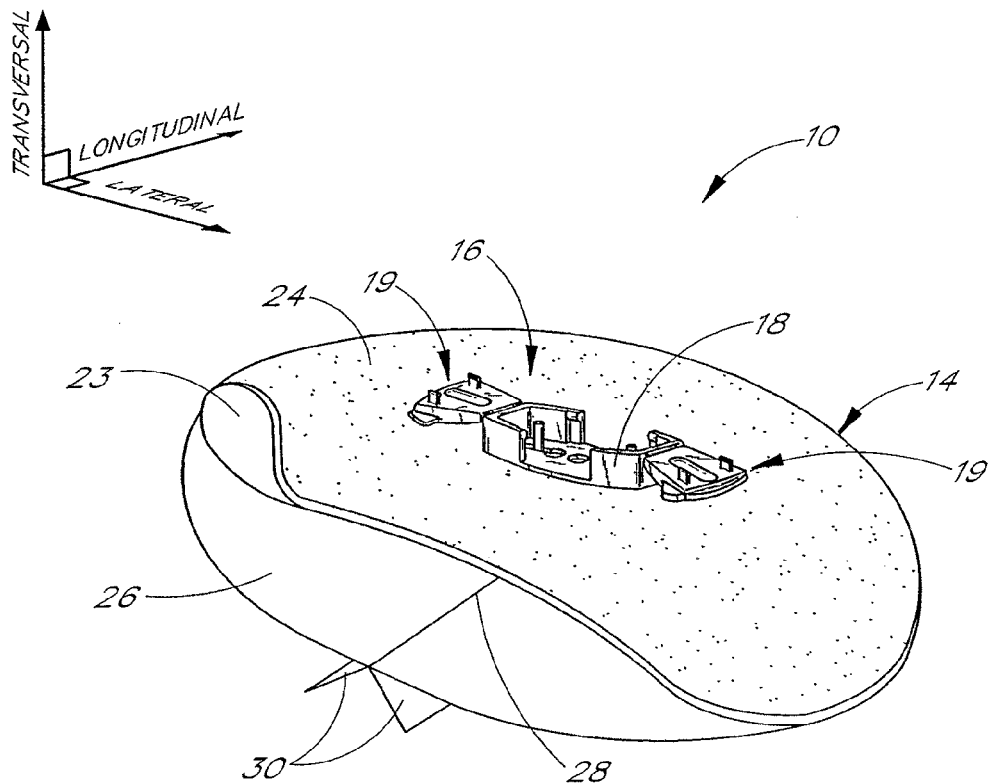
FIG. 1 is a perspective view of an anchoring system in accordance with a preferred embodiment of the present invention including a pair of movable posts and a pair of separate covers illustrated in an open position and with a corner of an anchor pad turned up to illustrate its lower surface.
Figure 2:
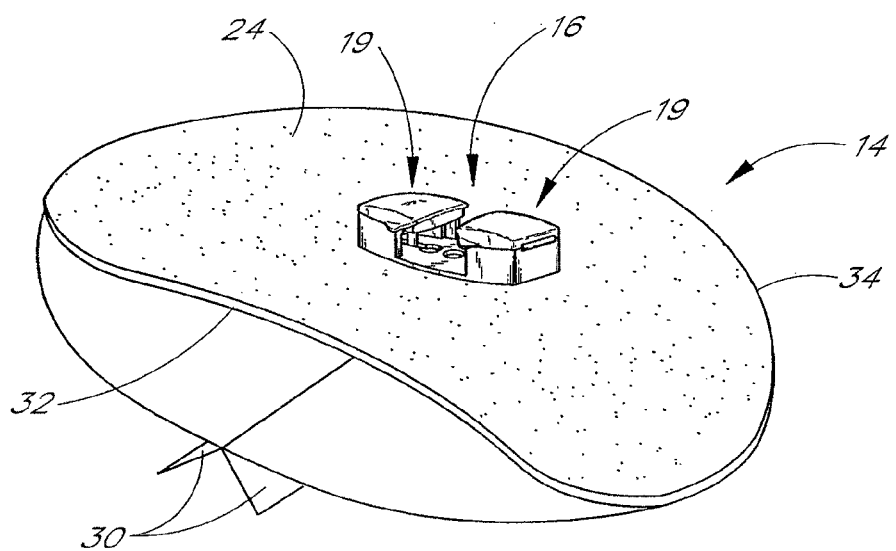
FIG. 2 is a perspective view of the anchoring system of FIG. 1 shown with the covers in a closed position.

With reference to FIGS. 1 and 2, the anchoring system 10 is constructed in accordance with a preferred embodiment of the present invention. The system comprises an anchor pad 14 and a retainer 16 that includes a base 18, a cover assembly 19 and at least one post. In the illustrated embodiment, the post is part of a post platform that is attached to the retainer base 18 when the retainer 16 is assembled. The post, as noted below, can be part of the base 18 and/or the cover assembly or be a separate individual piece. The retainer 16 is configured to accept and to retain and secure a section of a catheter 12 (shown in FIG. 3) within the anchoring system 10. Alternatively, the same arrangement can be used to secure a detachable catheter fitting which is attached to a catheter to be retained, as described below.

Figure 4:
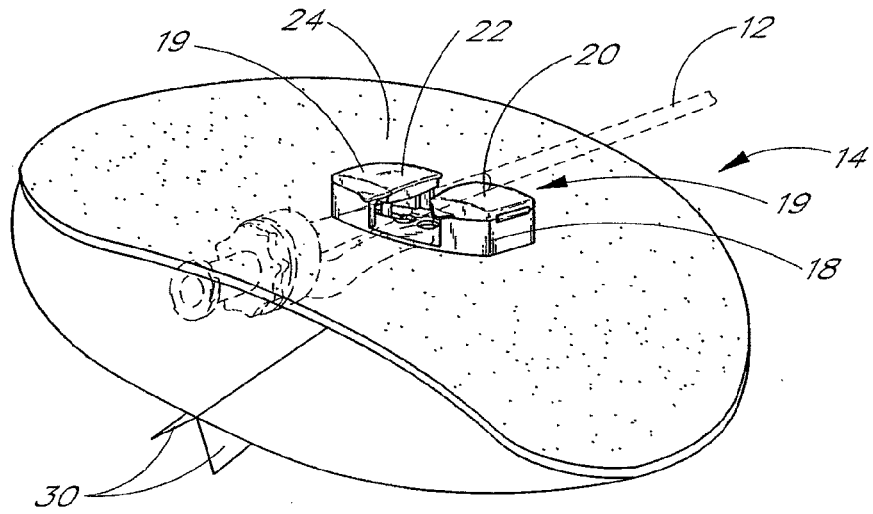
FIG. 4 is a perspective view of the anchoring system of FIG. 3 shown with the covers in the closed position and the exemplary catheter (again shown in phantom lines) positioned in and retained by the retainer.

As illustrated in FIGS. 3 and 4, the catheter 12 or fitting is inserted into the base 18 of the retainer 16 while the cover assembly 19 is in an open position, as shown in FIG. 3. As illustrated, the cover assembly 19 in the present embodiment comprises two separate covers 20, 22, each independently attached to the base 18. Once the catheter 12 or fitting is positioned on the base, the covers 20, 22 are moved into a closed position over the base 18 and catheter 12 to inhibit transverse motion of the catheter 12. This can be seen in FIG. 4. The catheter 12 or fitting also is retained laterally and longitudinally by its interaction with one or more posts of the retainer 16 and by its interaction with the surrounding sections of the base 18 and/or the covers 20, 22.

The retainer 16 is disposed upon an upper surface of the anchor pad 14. The lower side 23 of the anchor pad 14 includes an adhesive surface which adheres to the skin of the patient in order to maintain the position of the retainer 16, and hence the catheter 12, with respect to the patient.

As is seen in FIG. 1, the anchor pad 14 is a substantially flat piece of material with transversely opposing sides. The proximal or lower side 23 of the pad faces toward the skin of the patient, and is preferably covered with an adhesive surface suitable for attaching the anchor pad 14 to the skin of the patient. The upper or distal side 24 of the pad faces away from the skin of the patient and supports the retainer 16.

The anchor pad 14 preferably comprises a laminate structure with an upper foam layer (e.g., closed-cell polyethylene foam) and a lower adhesive layer. The lower adhesive layer constitutes the lower surface 23 of the anchor pad 14. The lower surface 23 desirably is a medical-grade adhesive and can be either diaphoretic or nondiaphoretic, depending upon the particular application. Such foam with an adhesive layer is available commercially from Tyco Adhesives of Norwood, Mass.

A surface of the upper foam layer constitutes the upper surface 24 of the anchor pad 14. The upper surface 24 can be roughened by chemical priming or corona-treating the foam with a low electric charge. The roughened or porous upper surface 24 can improve the quality of the adhesive joint (which is described below) between the base 18 and the anchor pad 14. In the alternative, the flexible anchor pad 14 can comprise a medical-grade adhesive lower layer, an inner foam layer and an upper paper or other woven or nonwoven cloth layer.

A removable paper or plastic release liner 26 desirably covers the adhesive lower surface before use. The liner 26 preferably resists tearing and desirably is divided into a plurality of pieces to ease attachment of the pad to a patient's skin. In the illustrated embodiment, the liner is split along a centerline 28 of the flexible anchor pad 14 in order to expose only half of the adhesive lower surface at one time.

The length of each liner piece, as measured in the lateral direction, extends beyond the centerline 28 of the anchor pad 14 and is folded over, or back onto the liner. This folded over portion defines a pull-tab 30 to facilitate removal of the liner piece 26 from the adhesive lower surface. A healthcare worker uses the pull-tab 30 by grasping and pulling on it so that the liner piece 26 is separated from the lower surface. The pull-tab eliminates the need to pick at a corner edge or other segment of the liner in order to separate the liner from the adhesive layer. The pull-tab 30 of course can be designed in a variety of configurations. For example, the pull-tab need not be located along a centerline of the anchor pad 14; rather, the pull-tab can be located along any line of the anchor pad 14 in order to ease the application of the anchor pad 14 onto the patient's skin at a specific site. For example, an area of a patient's skin with an abrupt bend, such as at a joint, can require that the pull-tab be aligned toward one of the lateral ends of the anchor pad 14 rather than along the centerline.

The anchor pad 14 also preferably includes a concave section 32 that narrows the center of the anchor pad 14 proximate to the retainer 16. In the illustrated embodiment of FIG. 2, the anchor pad 14 is formed generally into a crescent shape that includes a concave section 32 on one side of the retainer and a convex section 34 on the other. This shape permits the pad 14 to be placed on the patient such that the arms of the crescent extend away from the insertion site.

The retainer is preferably centered upon the anchor pad 14 about an axis which bifurcates the crescent shape. Consequently the lateral sides of the anchor pad 14 have more contact area, both forward and rearward of the retainer 16 in the longitudinal direction, which provides greater stability and adhesion to a patient's skin while still permitting the retainer 16 to be located near the insertion site. Although not illustrated, the anchor pad 14 also can include suture and/or breather holes to the sides of the retainer 16.

With reference now to FIGS. 5-8, the base 18 and the cover assembly 19 principally define the retainer 16. As noted above, the cover assembly 19, in the illustrated embodiment, comprises two covers 20, 22, each of which is connected to the base at a folding hinge 36. This arrangement allows the base 18 and the covers 20, 22 to be formed as a unitary piece. This can be accomplished by any of a variety of ways well known to those skilled in the art. For instance, the base 18 and the cover assembly can be injection molded in order to reduce fabrication costs. As shown in FIG. 5, one cover 20 is in a closed position, while the other cover 22 is in an open position.

As will become apparent, several features of the cover assembly and base 18 are desirably flexible. Suitable materials which are both sufficiently strong but flexible include without limitation: plastics, polymers, or composites such as polypropylene, polyethylene, polycarbonate, polyvinylchloride, acrylonitrile butadiene styrene, styrene butadiene, nylon, olefin, acrylic, polyester, moldable silicon, thermoplastic urethane, thermoplastic elastomers, thermoset plastics and the like. The retainer 16 is preferably formed by injection molding using a styrene butadiene polymer, such as KRO3 resin, available commercially from Phillips Petroleum of Houston, Tex. However, other materials can be used, and the retainer can comprise a multi-piece base or cover as well.

In the embodiment illustrated in FIG. 5, the base 18 includes an elongated body of a generally hollow, generally parallelepiped shape. The base 18 can be configured in a variety of shapes, however, such as circular, square, or trapezoidal, in order to suit a particular application. For example, the base 18 may be configured to generally match the shape of the anchor pad 14 (shown in FIG. 1) or the shape of the winged catheter fitting (not shown). In the illustrated embodiment, a parallelepiped shape is preferably used to allow the base 18 and covers 20, 22 to be integrally formed and to capture the somewhat rectangular shape of the catheter fitting wings (see FIG. 12).

As understood from FIGS. 5-7, a bottom wall 37 of the base 18 includes a substantially flat bottom surface 38 with the exception of a recess 40 that extends upward. The recess 40 extends laterally from one lateral side of the base 18 to the other along the bottom side 38 of the base 18, and has a longitudinal width and transverse depth sufficient to receive the post(s) and/or a post platform, as described below.

The base 18 also includes one or more openings to facilitate connection of the post(s) (described below) to the base 18. These holes extend through the bottom wall 37 of the base 18 and open into a hollow receiving space 42 defined within the retainer 16. In the illustrated embodiment, a central circular opening 44 is formed in the center of the recess 40; however, this opening can be disposed at other locations on the base 18.

As will be described in greater detail below, the retainer 16 includes at least one post, which in some modes of the invention is movable relative to the base 18. The base 18 accordingly includes at least one additional opening to receive the post. This opening can have a complementary shape to that of the post or can be enlarged relative to or have a different geometry than the shape of the post. In the mode of the invention where the post is movable, the opening desirably has a shape that is elongated in at least one direction so as to allow the post to move in such direction.

In the embodiment illustrated in FIGS. 1-12, the base 18 includes two additional openings 46 to receive two posts. While only a single post and hence a single opening is required, the illustrated embodiment uses two posts and two openings. Each post opening 46 is provided for a corresponding post such that the corresponding post protrudes through the bottom wall 37 of the base 18 when the retainer 16 is assembled. The retainer 16, however, can include more than two post-opening pairings in some applications of the present anchoring system, as will be understood by one of ordinary skill in the art.

Figure 8:
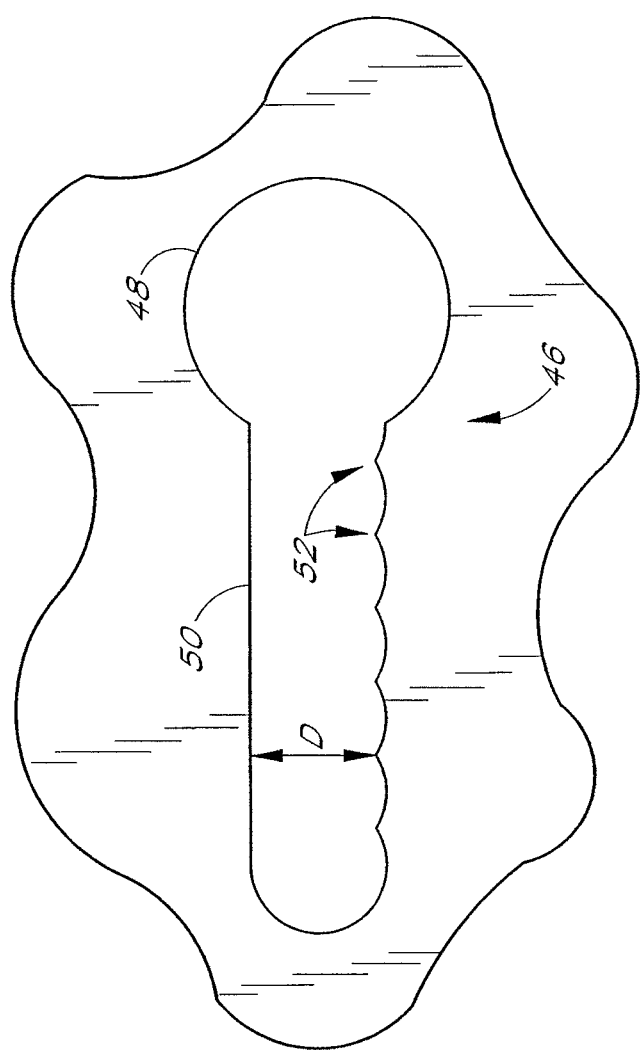
FIG. 8 is an enlarged view of the area encircled by line 8-8 of FIG. 5 and illustrates the structure of a post opening within the base of the retainer.

As best seen in FIGS. 5 and 8, each post opening 46 in the illustrated embodiment includes a substantially circular region 48 and an elongated slot 50 extending from the substantially circular region 48. The substantially circular region 48 has a diameter larger than the width of the elongated slot 50, and the elongated slot 50 has a width larger than the diameter of the corresponding post.

The present embodiment is configured with the slot 50 extending from the circular region 48 in a lateral direction in order to accommodate differing lateral spacing between mounting holes among different catheters or catheter fittings. As noted previously, however, these slots could also extend longitudinally or in a direction skewed relative to the longitudinal and lateral axes in order to suit a particular application. Also, the slot 50 in the illustrated embodiment extends from the substantially circular region 48 outwardly relative to the center of the base 18, but the circular region 48 can be located at other positions along the corresponding slot 50 (e.g., at the outer lateral end of the slot). In addition, more than one slot can extend from the circular region 48.

As best seen in FIG. 8, one edge of the slot has a scalloped shape. Each scallop has a radius of curvature generally matching a radius of a corresponding post that slides through the slot 50. The distance D between the lateral end point 52 of each scallop and the opposing edge of the slot 50 preferably is less than a diameter of the corresponding post so as to inhibit unintentional movement of the post within the slot 50, as described below.

As seen in FIGS. 5-7, the base 18 includes upstanding front and back walls 54, 56 that are spaced from the central opening 44 in the longitudinal direction, and extend upward from the lower wall 37 of the base 18. An opening 58, 60 generally bifurcates each wall 54, 56, respectively, to allow the catheter to pass through one wall 54, through the receiving space 42 and above the lower wall 37 of the base 18, and then out the opposite wall 56.

Sidewalls 62, 64 of the base 18 are spaced lateral from the central opening 44 and extend upward from the lower wall of the base 18. These sidewalls 62, 64 are continuous with the front and back walls 54, 56 of the base. The corners between the sidewalls 62, 64 and the front and back walls 54, 56 preferably are rounded.

The base 18 has an open upper end that is generally defined by the upper edges of the walls 54, 56, 62, 64. Thus, while not truly parallelepiped, the retainer 16 does have a generally rectangular box-like shape without an upper wall and with the central openings 58, 60 formed in the front and back walls 54, 56.

The base 18 also includes holes 66 which allow portions of the front and rear walls 54, 56 of the base 18 to flex in a longitudinal direction more easily. This feature is advantageous to the operation of the latching mechanism, described below.

The longitudinal, lateral and transverse dimensions of the retainer 16 desirably are as small as possible, while still receiving and stabilizing the catheter 12, including its wings. In particular, the longitudinal dimension of the base 18, which is defined between the front and back walls 54, 56, preferably is long enough to stabilize the retained length of catheter 12. That is, the length of catheter 12 which is secured within the retainer 16, is sufficient to inhibit rocking of the catheter 12 relative to the retainer 16. The longitudinal dimension of the base 18 also is sufficient to receive the largest length of catheter wings for which the retainer 16 is designed.

The lateral dimension of the base 18, which is defined between the sidewalls 62, 64, similarly is sized to accommodate the largest width of catheter wings for which the retainer 16 is designed. It is also preferred that the lateral dimension be sufficient to provide a convenient and natural grip of the base 18 of the retainer 16 while manipulating the covers 20, 22 and/or posts of the retainer 16. The lateral dimension also preferably provides sufficient width to mount hinges and latch mechanisms in the present embodiment, as described below.

The transverse height of the base 18 preferably corresponds to the thickest catheter wing for which the retainer 16 is designed. While the catheter body may have a larger size than its wing thickness, the base 18 accommodates this through its open central region between the covers 20, 22. The base 18 thus needs not have a greater transverse height than that of the catheter 12, and consequently, the profile of the retainer 16 is minimized.

The receiving space 42 is formed on the base 18 between the lateral walls 62, 64 of the base 18. The receiving space 42 is desirably formed so as to accept and retain a portion of the catheter or catheter fitting, and in particular the wings thereof, without occluding the lumen of the catheter.

As seen in FIGS. 5 and 7, the covers 20, 22 have a size and shape that desirably is coextensive with the longitudinal dimension of the base 18. Although each cover 20, 22 preferably extends longitudinally at least as far as the base does, the cover 20, 22 need not span the entire lateral dimension of the base. This will be discussed below. In some modes it is desirable for the covers 20, 22 to be larger longitudinally than the base 18. By protruding beyond the longitudinal dimension of the base 18, the covers 20, 22 can also include a flange 68 that is useful in operation of the latch mechanism of the cover. This will be discussed below. In other modes, the cover need not include the flanges 68.

Each cover 20, 22 preferably is connected to the base 18 by at least one hinge 36 to provide each cover 20, 22 with at least two positions: an open position, in which the receiving area 42 of the base 18 is exposed and into which a catheter or fitting may be inserted; and a closed position, in which the cover 20, 22 is located over the base 18 and covers at least a portion of the receiving area 42. In the closed position, the covers 20, 22 are held in place by a latch mechanism, described below, to inhibit the unintentional transverse release of the catheter or catheter fitting from the receiving area 42 of the base 18. The covers desirably are sufficiently sized to accommodate the necessary latch mechanism components and to extend over or around at least a portion of the posts 70 (and possibly receive upper ends of the posts) when in the closed position. As explained in greater detail below, the interaction between the upper portions of the posts 70 and the covers 20, 22 inhibits movement or play of the post upper ends relative to the covers 20, 22. Consequently, this interaction inhibits the posts 70 from deflecting or bending, at least in the longitudinal direction, when the catheter is tugged to maintain a secure connection between the posts 70 and the catheter 12.

In the embodiment shown in FIGS. 5-7, each cover 20, 22 of the cover assembly 19 has a hinge 36 and a latch mechanism, such that each cover can be independently placed into an open or a closed position. In this embodiment, the covers 20, 22 do not contact one another when both are in the closed position, as shown in FIGS. 2 and 4. Although both covers extend from the lateral sides 62, 64 of the base 18 toward the center of the retainer 16, by reducing the lateral dimension of the covers 20, 22 such that the components do not interact when closed, it becomes possible to effectively secure catheters or fittings that extend transversely beyond the height which could be contained below the covers if the covers were to meet. By allowing such "centrally bulky" catheters or fittings to be accepted, the anchoring system 10 is more universal and has a lower profile as noted above. An example of how the retainer 16 and posts hold a catheter 12 is shown in FIG. 4.

On each cover 20, 22, a recess 72 is formed which will lie over the post opening 46 on the corresponding half of the base 18 when the cover is in the closed position. This recess 72 preferably extends from a point directly above the substantially circular region 48 of the post opening 42 and along the length of the elongated slot 50 of the corresponding post opening. The recess 72 desirably is deep enough and wide enough along its length to freely receive the upper end of the corresponding post 70, which protrudes through the corresponding post opening 46, such that the post 70 does not interfere with the movement of the cover 20, 22 into the closed position. The recess 72 also receives the upper end of the post 70 when the cover 20, 22 is closed to inhibit the post 70 from bending in the longitudinal direction. Of course, in some applications, the post 70 can extend through the cover 20, 22 without interfering with movement of the cover and with the cover capturing a portion of the post to inhibit bending of the post in the longitudinal direction.

As can be seen in FIG. 7, the covers 20, 22 are coupled to the base 18 by flexible couplings or hinges 36. Each hinge 36 preferably comprises a flexible band that can take any number of forms to mechanically connect the cover 20, 22 to the base 18 while permitting pivotal movement of the cover 20, 22 relative to the base 18 so as to enable engagement or disengagement of these parts, as described below.

In the illustrated embodiment, the band is formed of flexible material, desirably of the same material from which the base 18 and cover 20, 22 are comprised. Advantageously, the hinges 36 are integrally molded with the base 18 and the covers 20, 22 to form a unitary member, as noted above. The hinges 36 are located at an outer edge of the base 18 and the cover assembly 19; however, the hinges 36 need not be laterally located at an extreme end of the base 18 or cover assembly 19. The illustrated embodiment shows the hinges 36 positioned near the same plane as the upper edges of the base 18 for ease of manufacture.

As best understood from FIG. 5, the width of the hinges 36, as measured in the longitudinal direction, is desirably less than that of either the base 18 or the covers 20, 22 to allow some leeway or play when engaging or disengaging the cover 20, 22 to the base 18. That is, this shape allows the hinge 36 to twist to some degree to compensate for some manufacturing tolerances; however, the hinges can have at least as large of a longitudinal dimension as the base 18 and/or the covers 20, 22.

The hinges 36 are desirably integrally formed along common corresponding exterior surfaces of the covers 20, 22 and base 18. Each hinge 36 has a generally U-shape 74 when the cover is closed, and extends from both the base 18 and the cover 20, 22 in the lateral direction to the side of the retainer 16. A gap, corresponding to a transverse height of the hinge 36, exists between the base 18 and covers 20, 22. This gap, however, can be reduced or eliminated from the retainer for some applications by using a different hinge design.

The hinges 36 enable each cover 20, 22 to move between the open position and the closed position. The open position, shown by cover 22 in FIGS. 5 and 7, is characterized by exposing the corresponding post in the transverse direction. When both covers are in the open position, as shown in FIG. 3, the retainer 16 is capable of receiving a portion of the catheter 12. The closed position, shown FIGS. 4, 5 and 7, is characterized by the cover 20 lying in contact or in near contact with the base 18 so as to position the post within the recess 72 in the cover 20. When both covers 20, 22 are in the closed position, as shown in FIG. 4, the retainer 16 surrounds the received portion of the catheter 12.

The hinges 36 need not provide 180° of movement for the covers 20, 22 relative to the base 18 to establish a closed position and a fully open position. For instance, the hinges 36 can permit a smaller degree of movement (e.g., 90°) between the base 18 and the covers 20, 22 while still providing enough space to transversely insert the catheter 12 into the retainer 16 when both covers 20, 22 are open.

To hold the covers 20, 22 to the base 18 and to effectively retain the catheter 12 or catheter fitting within the retainer 16, the base and cover include structures that interengage when the covers are in the closed position. As can be seen in FIG. 6, a latch mechanism 80 is provided for securing the covers 20, 22 in the closed position relative to the base 18. The latch mechanism 80 comprises at least one movable keeper 82 and at least one latch 84. In the illustrated embodiment of FIG. 6, the keeper 82 is disposed on the cover 20 while the latch 84 is disposed on the base 18. However, those skilled in the art will recognize that the keeper can be disposed on the base and the latch can be disposed on the cover.

Each keeper 82 extends from the cover 20 toward the base 18 of the retainer 16 from the lower side of the cover 20 ("lower" as seen when the cover is in the closed position as in FIG. 6). In addition to extending from the cover 20, each keeper 82 has at the end farthest from the cover a tang 86 that extends in the direction toward the corresponding latch 84. This tang 86 is rounded as seen in FIG. 6; however, the tang can have a surface that lies generally normal (e.g., ±15° from perpendicular) to the transverse axis.

The latch 84 comprises a protrusion 88 that is formed on the base 18 at a location that will interact with the tang 86 of the keeper 82 when the cover 20 is in the closed position. This can be seen in FIG. 6. In the illustrated embodiment, a protrusion 88 is formed on the front and back walls 54, 56 of the base 18. The latch 84 is located along the wall 54, 56 of the base at a position adjacent to a hole 66 in the base 18. By positioning the latch 84 at such a location, it is more able to flex in the longitudinal direction. This is because the hole 66 reduces the resistance of the base 18 in that region to deformation.

As the cover 20 is moved into the closed position, the keeper 82 will flex as the tang 86 moves past the protrusion 88 of the latch 84, and then will relax or spring back into its original state once the tang 86 has moved past the protrusion 88. This will prevent the cover 20 from unintentionally moving out of the closed position. The lower side of the protrusion 88 preferably has a complimentary shape to that of the top of the tang 86 to promote engagement between them when the cover is closed. In the illustrated embodiment, the protrusion 88 is preferably rounded in the same manner as the tang 86 of the keeper 82. In another variation, the protrusion has a generally flat lower surface that is upwardly included at about 10° relative to the plane of the bottom wall 37 and the upper surface of the tang 86 has a similar complimentary surface that slopes downward by 10°.

In order to allow disengagement of the latching mechanism 80, it is necessary for the keeper 82 to flex as the tang 68 moves past the protrusion 88 of the latch 84. In one mode of operation, this can be accomplished by pressing upon a flange 68 or other extension of the cover 20. By pressing upon the flange 68, the cover 20 bends, moving the tang 86 of the keeper 82 away from the protrusion 88 of the latch 84, and allowing the cover 20 to be moved out of the closed position without exerting excessive force upon the cover. Desirably, such a flange 68 is formed integrally with the cover 20 of the retainer 16. The reduced thickness of the cover 20 along its center section, which is created by the recess 72, aids in the cover bending in this manner.

As best seen in FIG. 7, each cover 20, 22 also includes an overhang 90 formed on its inner edge (i.e., the edge closest to the central opening 44). This overhang 90 preferably is sized to allow the fingertip or fingernail of the healthcare worker to slip underneath the overhang to pull up the cover 20, 22 in another mode of opening the cover. The upward force applied causes the tang 86 to slide over the protrusion 88 to disengage the latching mechanism 80. As a result, the overhang 90 provides another way to open the cover 20, 22.

In the illustrated embodiment, each cover 20, 22 has two keepers 82, requiring two latches 84 on the base. The latch mechanisms 80 on each cover are formed as mirror images of each other.

Figure 10:
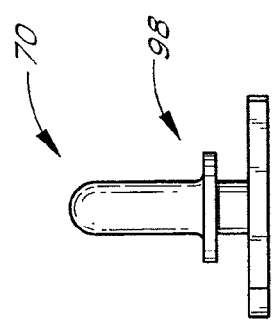
FIG. 10 is a side elevational view of the post platform of FIG. 9.
Figure 9:
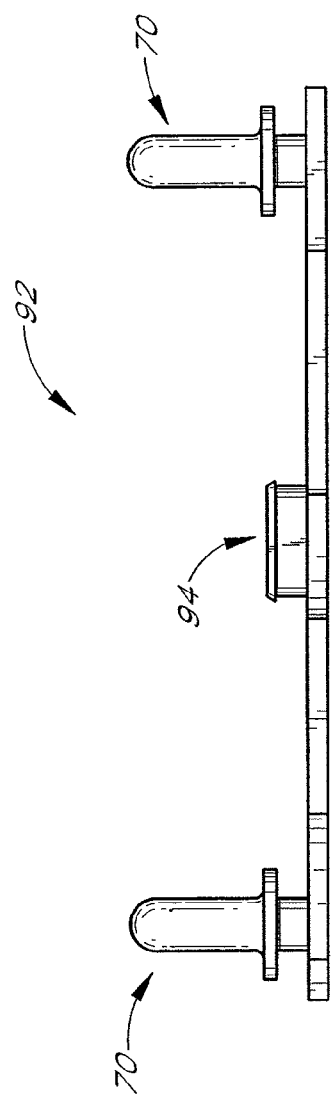
FIG. 9 is a front elevational view of a post platform of the retainer of FIG. 1.
Figure 11:
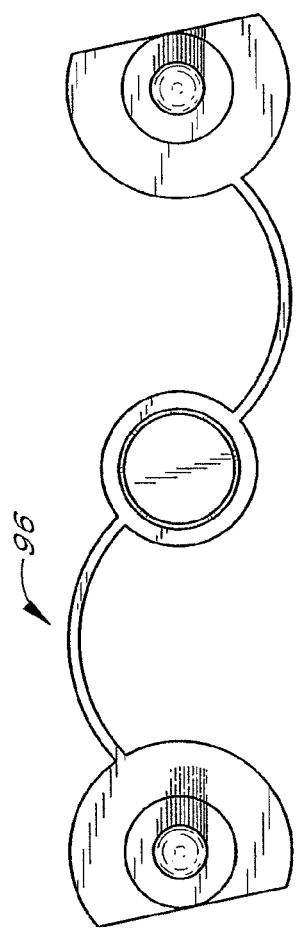
FIG. 11 is a top plan view of the post platform of FIG. 9.

In order to aid the manufacture and assembly of the retainer, the posts may be formed as part of a post platform 92. An embodiment of the post platform 92, which includes a plurality of movable posts 70, is illustrated in FIGS. 9, 10 and 11. The post platform 92 includes an attachment button 94 for connecting the platform 92 to the base 18, posts 70 that are configured to extend through the post openings 46 in the base 18, and connectors 96 which at least initially hold the posts 70 to the attachment button 94. In the illustrated embodiment, the platform 92 is attached to the base 18 from below by aligning the attachment button 94 with the central opening 44 in the base 18, inserting the posts 70 through the post openings 46, and pressing the platform 92 upward into the recess 40 on the lower side of the base 18. When fully inserted, the larger radius on the upper portion of the attachment button 94 will snap into position in the central circular opening 44. In one variation, the upper portion of the attachment button 94 can be disposed within a countersink formed on the upper side of the bottom wall 37. The pair of posts 70 then protrudes through the post openings 46 of the base, and may move laterally within the lateral extent of their respective post openings 46 in the base 18.

While the present embodiment shows posts 70 that are connected to the attachment button 94 and to each other, this arrangement is not necessary for advantageous operation of the retainer. Those of ordinary skill in the art will appreciate that the connected arrangement of the posts 70 on the platform 92 is largely to facilitate manufacture and construction of the retainer.

The attachment button 94 comprises a cylindrical peg of a diameter to allow it to be inserted through the central circular opening 44 of the base 18 from the lower, or proximal, side. A distal portion of the cylindrical peg has a larger radius than the proximal portion of the attachment button. This upper portion is also of slightly larger radius than the central circular opening 44 in the base 18. The upper edge of the attachment button 94 is preferably chamfered to allow the button to be easily inserted through the central circular opening 44 of the base. Once inserted into the central circular opening, the larger radius at the distal portion of the button 94 will prevent the button from being pulled out of the base 18 in the proximal direction.

The connectors 96, illustrated in FIG. 11, comprise extensions from the lowest portion of the attachment button 94 which extend laterally therefrom and connect to the lowest portion of the posts 70. Desirably, these connectors 96 allow the distance at which the posts 70 are disposed from the attachment button 94 to vary after the retainer is assembled.

One way to accomplish this is illustrated in the embodiment of FIGS. 9, 10 and 11. Each connector 96 comprises a leash that extends parallel to the base 18 of the retainer away from the attachment button 94 at an angle to the lateral direction. The leash can be straight when fully extended or can follow a semi-looped or curved path. This path can also assume a zigzag or similar shape. The shape of the leash allows the lateral extension of the leash to be adjusted by permitting the leash to flex. In the illustrated embodiment, each connector 96 can have enough flexibility to allow it to remain intact while spanning distances ranging from the farthest lateral position in the post opening 46, to the minimum lateral distance defined by the circular portion 48 of the post opening. In the illustrated embodiment, this is accomplished by allowing the leash to bend and fold back upon itself. In a variation, the leashes can be configured to bias the posts 70 inward or outward. In another variation, however, once the posts 70 are assembled in the base, the posts do not need to be tethered together, and the leashes can be designed to break after assembly.

One of the posts 70 is disposed at the lateral end of each connector 96. The posts 70 comprise substantially cylindrical members that extend transversely in the distal direction from a lowest portion that is attached to the corresponding connector 96 of the post platform 92. The posts 70 desirably also include a flange 98, located distally along the length of the cylinder such that it will lie above the bottom wall 37 of the base 18 when the platform 92 is inserted into the retainer base 18. This flange 98 is preferably sized to have a radius larger than the radius of the elongated slot 50 portion of the post opening 46, but smaller than the circular section 48 of the post opening 46. In this manner, the flange 98 can be inserted through the circular section 48 of the post opening 46 along with the post 70, and then remain above the base 18 of the retainer when the post 70 is moved to a position along the length of the elongated slot 50. The flange 98 stabilizes the post 70 and maintains its proper orientation with regard to the base 18, i.e., the flange 98 maintains the post 70 in a transversely upright position and inhibits significant rocking of the post.

Figure 11A:
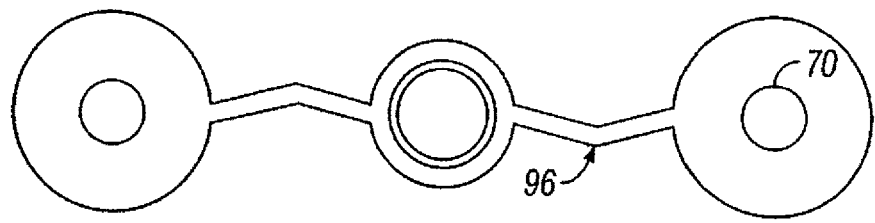
FIG. 11A is a top plan view of an alternate post platform for use with the retainer of FIG. 1.
Figure 11B:
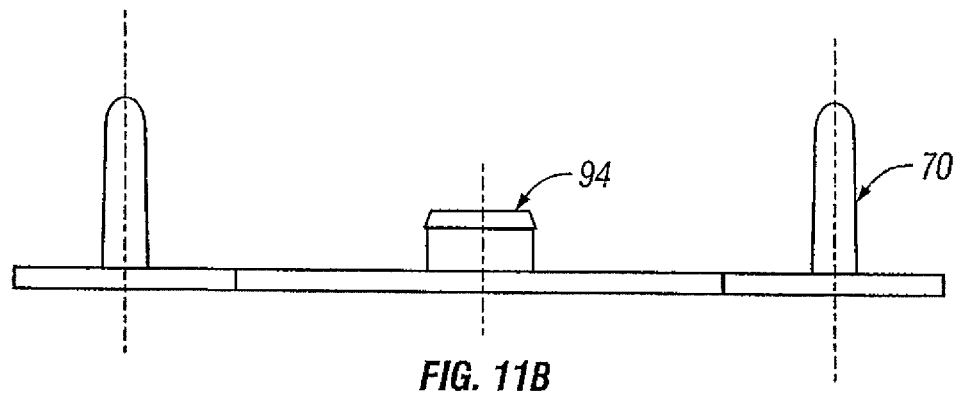
FIG. 11B is a front elevational view of the post platform of FIG. 11A.
Figure 11C:
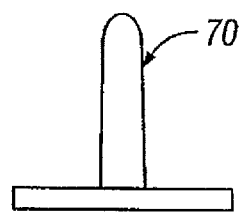
FIG. 11C is a side elevational view of the post platform of FIG. 11A.
Figure 13:
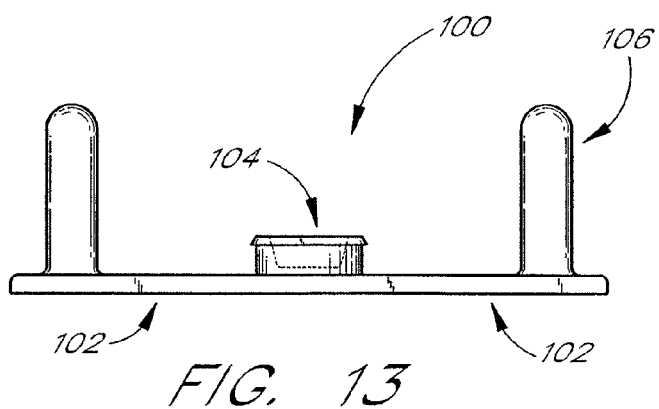
FIG. 13 is a front plan view of another post platform using fixed position posts, suitable for use with the base and cover of FIG. 1.
Figure 14:
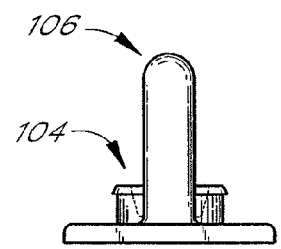
FIG. 14 is a side elevational view of the fixed post platform of FIG. 13.
Figure 15:
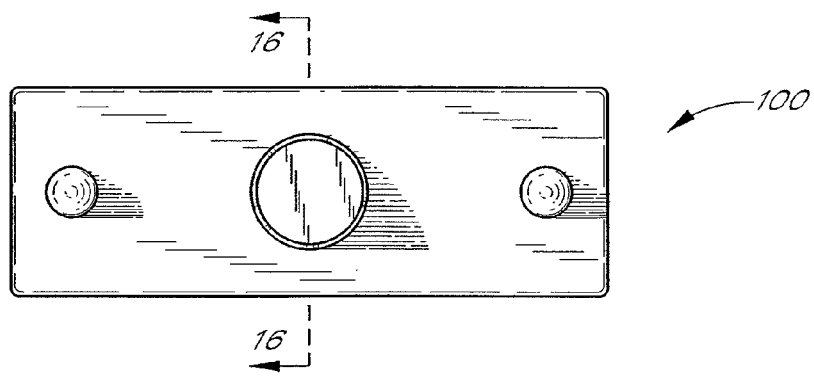
FIG. 15 is a top plan view of the fixed post platform of FIG. 13.
Figure 16:
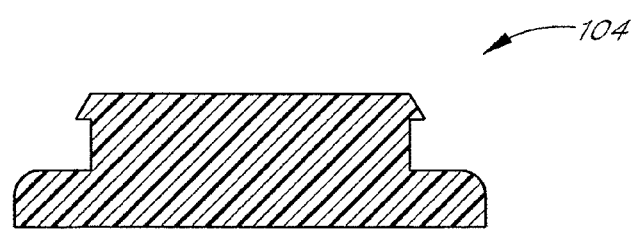
FIG. 16 is a cross-sectional view of the fixed post platform of FIG. 15 taken along line 16-16.

It is also possible to make use posts which do not possess a flange. An example of such a post platform is shown in FIGS. 11A-11C. This post platform is used in substantially the same manner as the platform 92 shown in FIGS. 9-11, but does not make use of flanges to stabilize the posts. Such flange-less posts are suitable for use with bases in which the post openings 46 do not include circular regions 48, but only consist of an elongated slot 50. An example of such a base is shown and discussed below.

The circular region 48 of the post opening 46 is located at the innermost lateral position that a post 70 would be desirably located, and the track 50 extends to the outermost lateral position that a post 70 would be desirably located. By moving the post laterally, it can be positioned as desired at any location along the length of the slot 50. Along the length of the slot 50 are positioned the series of protrusions or scallop end points 52 which extend into the slot 50 and effectively narrow the width of the slot at the position of each protrusion 52, as noted above. At the locations of the protrusions 52, the width of the slot 50 is comparable to, or slightly narrower than, the width of the posts 70 which will extend through the post opening 46. This arrangement provides a ratcheting action for positioning the post 70 at the desired location, and then retaining the post at said location.

Because the material of the base 18 and post 70 are slightly elastic, it is possible to push the post along the slot 50 past a protrusion 52 into the section of the slot that is wider between the protrusions, even if the width of the slot at the protrusion is slightly narrower than the diameter of the post 70. However, once in the desired position along the length of the slot 50, the protrusions 52 will inhibit unintended lateral motion of the post 70 from its location. This ratcheting arrangement allows effective positioning of the posts 70 to any desired lateral position between protrusions 52 without undesirable inadvertent motion of the posts once positioned.

Although the number of posts 70 shown in the instant embodiment is two, any number of posts may be used to accommodate a specific purpose. For example, if a particular catheter fitting contained four holes, a retainer designed to retain that fitting would desirably have four posts extending through four post openings in the base of the retainer. Similarly, if a "Y" shaped catheter or fitting was to be retained, three posts could be used to provide the desired stability.

The post 70 and/or the post platform 92 can be formed from a variety of materials using various known manufacturing methods. For example, the post 70 and/or post platform 92 can be injected molded. Suitable materials for such include without limitation: plastics, polymers, or composites such as polypropylene, polyethylene, polycarbonate, polyvinylchloride, acrylonitrile butadiene styrene, styrene butadiene, nylon, olefin, acrylic, polyester, moldable silicon, thermoplastic urethane, thermoplastic elastomers, thermoset plastics and the like. The posts and post platform 92 are preferably formed by injection molding using a nylon, such as Zytel 101 L, available commercially from E.I. du Pont Company of Wilmington, Del. However, other materials can be used, and the post platform can comprise a multi-piece assembly.

After the post platform 92 has been attached to the retainer base 18, the retainer 16 then is attached to the upper surface 24 of the anchor pad 14. The base 18 desirably is secured to the upper surface 24 by a solvent bond adhesive, cyanoacrylate or other bonding material. One such adhesive is available commercially as Part No. 4693 from the Minnesota Mining and Manufacturing Company (3M). With certain types of polymer (e.g., a styrene butadiene polymer), a UV cured adhesive also can be used, as known in the art. It is important when attaching the base 18 to the anchor pad 14 that the post platform 92 is not secured to the anchor pad as well. The posts 70 in this mode must be free to slide within the recess 40 on the underside of the base 18 and within the post openings 46 for the posts 70 to be properly movable between different desired locations.

The anchoring system 10 can optionally include a fitting for mounting the catheter to the retainer 16. If used, the fitting can take the form of a conventional box clamp and a soft wing clamp. Box clamps and soft wing clamps are commercially available from Arrow® for use with its CVC. Other clamps with suture wing extensions are currently in commercial use with Quinton® Hemodialysis catheters Cook® PICC's, Baxter® CVCs and B. Braun® CVCs. Those skilled in the art will find application for the present invention with any of these or other clamp configurations. As will be clear from a discussion below, the fitting can also be replaced with an inter-line connector or adaptor, such as those used to connect the catheter to a supply, delivery or drainage line.

When the anchoring system 10 is assembled as described above, the receiving space 42 formed between the base 18 and covers 20, 22 when they are in the closed position defines a channel. The channel is capable of receiving a portion or length of the catheter and is generally configured to house, grip and secure the affected catheter portion. In the illustrated embodiment, the channel has a generally symmetrical shape. However, other cross-sectional shapes may be used for particular applications, such as for supporting a Y-site catheter.

Although the shape of the channel may vary depending upon its application (i.e., depending upon a shape of the retained portion of the medical article for which the retainer is designed to be used), the length of the channel, as mentioned above, is desirably sufficient in the longitudinal direction to stabilize the catheter, rather than acting as a fulcrum for the catheter, as was discussed above. That is, the retainer 16 receives a sufficient length of the catheter to inhibit movement of the catheter in the lateral, longitudinal and transverse direction (i.e., to inhibit yaw, pitch and axial movement of the catheter), without kinking the catheter.

The internal width of the channel can be varied by adjusting the position of the posts 70. By moving or sliding the posts along their slots 50, the distance between the posts can be varied. This is especially important when the anchoring system 10 is used with a wide variety of catheters and catheter fittings that may not have similar juncture configurations or suture hole spacing.

With the covers 20, 22 in the closed position, a section of the catheter 12 is captured within the retainer 16. Thus, the retainer at least restricts, if not prevents, transverse and lateral movement of the retained section of the catheter. Transverse movement is also restricted when the covers 20, 22 are open by the height of the posts 70, which inhibit upward migration of the catheter 12 and/or catheter fitting. Inhibiting movement of the catheter in the longitudinal direction when the catheter 12 is secured within the retainer 16 is desirably accomplished by the posts 70 and holes.

Operation

In operation, as best seen in FIGS. 3, 4, and 12, the covers 20, 22 are moved toward the closed position. The relatively thin strip of material forming the hinge 36 allows the hinge to bend when finger pressure is exerted on the covers to close them. The tangs 86 at the end of the keepers 82 contact the protrusions 88 of the latches 84 on the base 18 when the covers 20, 22 near their closed position. Continued pressure forces the keepers 82 inward (toward each other) to permit the tangs 86 to pass beyond the protrusions 88. The tangs 86 snap over the protrusions 88 under the spring force provided by the deflected keepers 82 when the covers 20, 22 sit atop the base 18. The interaction between the tangs 86 and the corresponding surfaces of the latches 84 hold the covers in this position.

To open the latch mechanism 80, a healthcare worker presses inwardly on the protruding flanges 68 of the covers 20, 22 or lifts up the covers 20, 22, as described above. The resulting inwardly directed force deflects the keepers 82 and moves the tangs 86 inward to clear the protrusions 88 of the latches 84. The healthcare worker can then open the covers and expose the posts 70 and the base 18.

This releasable engagement between the covers 20, 22 and the base 18 allows the same retainer 16 to be used for an extended period of time, while permitting repeated attachment and reattachment of the catheter 12 or fitting to the anchoring system 10. In addition, the hinges 36 which connect the covers 20, 22 to the base 18 ensure that the covers will not be lost or misplaced when the catheter 12 is detached from the anchoring system 10. The healthcare worker wastes no time in searching for a misplaced cover, or in orienting a cover prior to latching, and he or she is not required to carry a separate instrument to detach the catheter from the anchoring system.

A healthcare worker may secure a catheter (or other medical article) to a patient using the above-described anchoring system (or a readily apparent modification thereof). The healthcare worker first opens the retainer 16 to expose the posts 70. Once opened, a catheter 12 may be transversely aligned over the posts 70, as shown in FIG. 3 and FIG. 12. The catheter 12 may then be placed into the channel formed between the posts 70. Optionally, openings formed on either the catheter 12 or a fitting can then be slid over the posts to further secure the catheter to the retainer 16. Once the catheter is so secured by the posts, the covers 20, 22 are closed and latched in the manner described above, as seen in FIG. 4.

If the catheter 12 is pulled in the longitudinal direction, the holding effect of the posts 70 and holes prevent the catheter from pulling through the retainer 16. The retainer thus inhibits longitudinal movement of the catheter relative to the retainer. Interaction between the base 18, covers 20, 22, posts 70 and holes restrict movement of the catheter 12 in the transverse and lateral directions. The interaction between the posts 70 and the covers 20, 22 also inhibits significant bending of the post upper ends in the longitudinal direction which, if allowed, would permit the catheter to slide off the posts.

Importantly, the base 18 and covers 20, 22 do not crimp or kink the catheter body when it is inserted within the channel and about the posts 70. Moreover, although the posts do bear against the catheter body, their limited pressure does not significantly occlude the corresponding catheter lumen(s).

Fixed Position Post Platform

A variation to that described above is produced using the same anchor pad 14, base 18 and covers 20, 22, but substituting a different post platform 100 for that described above. Specifically, the post platform of this alternate embodiment does not provide for movable posts; the posts are in fixed positions on the platform, and therefore, the user cannot adjust the spacing of the posts.

An example of a post platform 100 consistent with the present embodiment can be seen in FIGS. 13 to 16. The platform 100 still consists of connectors 102, an attachment button 104, and posts 106. However, instead of the connectors being flexible leashes that allow the distance between the post 106 and the attachment button 104 to be adjusted, the connector 102 comprises a lateral extension of the lowest portion of the attachment button 104 that also acts as the lowest portion of each post 106. Because there is no need for flexibility, the geometry of the connector is simplified. This fixed post arrangement also provides for greater stability for the posts 106 than the movable position post platform 92 does. It is most significant to note that in such an embodiment there is no need for the flange 98 described with reference to FIGS. 9 and 10 above. Not only is this flange not needed to provide longitudinal and lateral stability to the post 106 as it extends through the base 18, but the presence of such a flange would actually prevent the insertion of the post platform 100 into the base 18 in any case where the posts 106 were not positioned directly beneath the circular region 48 of the post opening 46. By eliminating the flange 98, the fixed position post platform 100 may be manufactured with any spacing desired between the posts 106, as long as the position of the posts falls somewhere along the length of the post opening 46 in the base 18 of the retainer 16.

The greater stiffness and stability provided by producing a fixed position post platform 100 allows the retainer 16 to be more easily assembled. While it also eliminates the possibility of adjusting the position of the posts 106 to accommodate different sized catheters or catheter fittings, it allows a simpler design to be used when the locations of the posts are known in advance to be at a fixed position.

Figure 17:
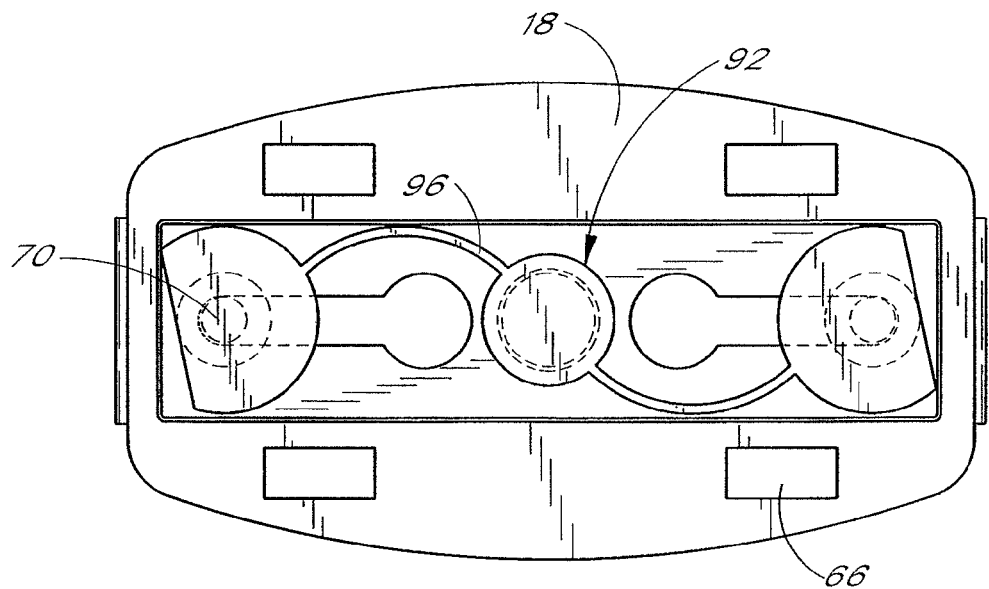
FIG. 17 is a bottom plan view of the assembled retainer of FIG. 1, showing the placement of the movable post platform of FIG. 9 within the groove of the retainer base.
Figure 18:
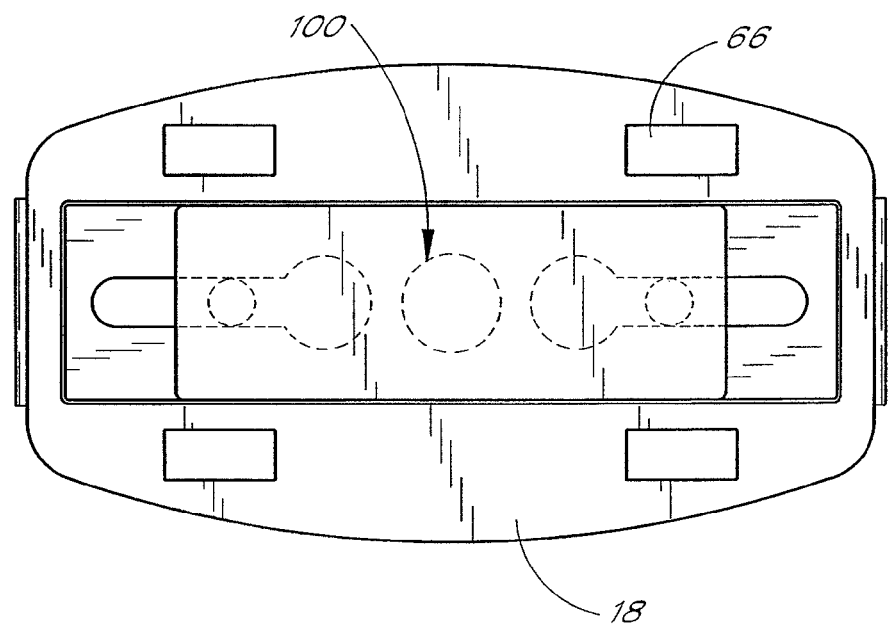
FIG. 18 is a bottom plan view of an assembled retainer using the fixed post platform of FIG. 13 within the groove of the retainer base.

Additionally, the use of a fixed position post platform 100 simplifies the process of adhesively attaching the base 18 to the anchor pad 14 because there is no need to avoid attaching the underside of the post platform 100 to the anchor pad 14. Compare FIGS. 17 and 18. In the movable post arrangement, shown in FIG. 17, the post platform 92, and particularly the connectors 96, must be free to flex and extend in order for the posts 70 to move. However, in the fixed position post platform 100 (shown in FIG. 18), no motion is possible. Therefore it is acceptable and even desirable for the post platform 100 to be bonded to the anchor pad 14 in the same manner as the base 18 of the retainer is attached to the anchor pad 14.

The fixed position post platform 100 can be formed of any of the materials noted above in connection with the movable post platform 92. The fixed position post platform 100 in a preferred embodiment is injected molded of a Lexan polycarbonate available commercially from General Electric Company, as Part No. 144R.

Single Movable Post Retainer System

Figure 19:
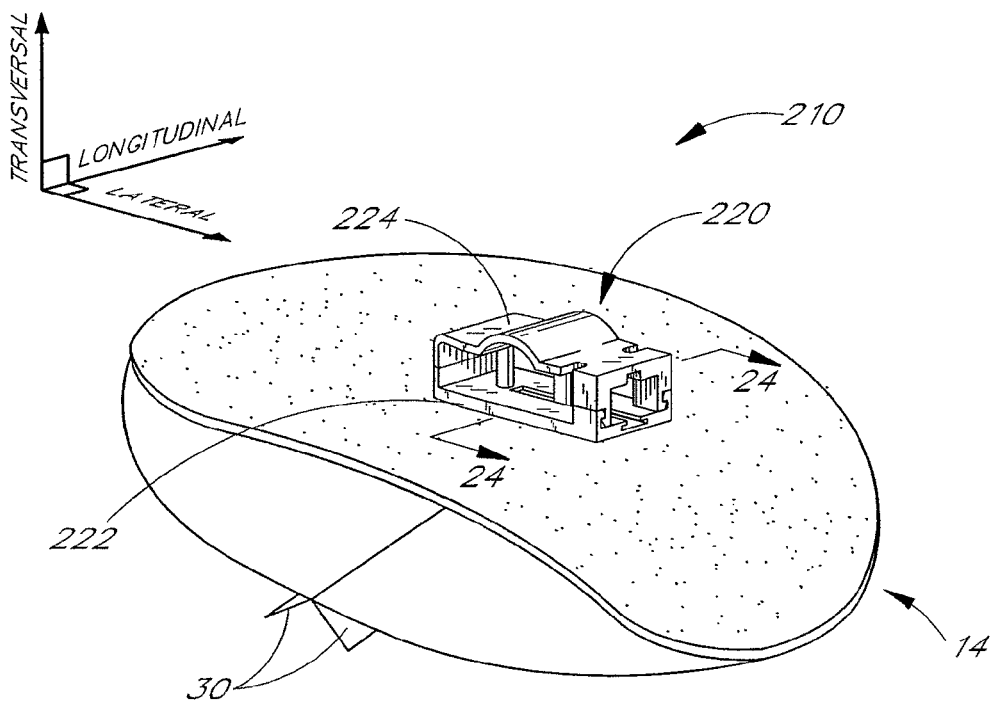
FIG. 19 is a perspective view of an anchoring system in accordance with an additional preferred embodiment of the present invention including a fixed post and a movable post, with the cover in a closed position.
Figure 20:
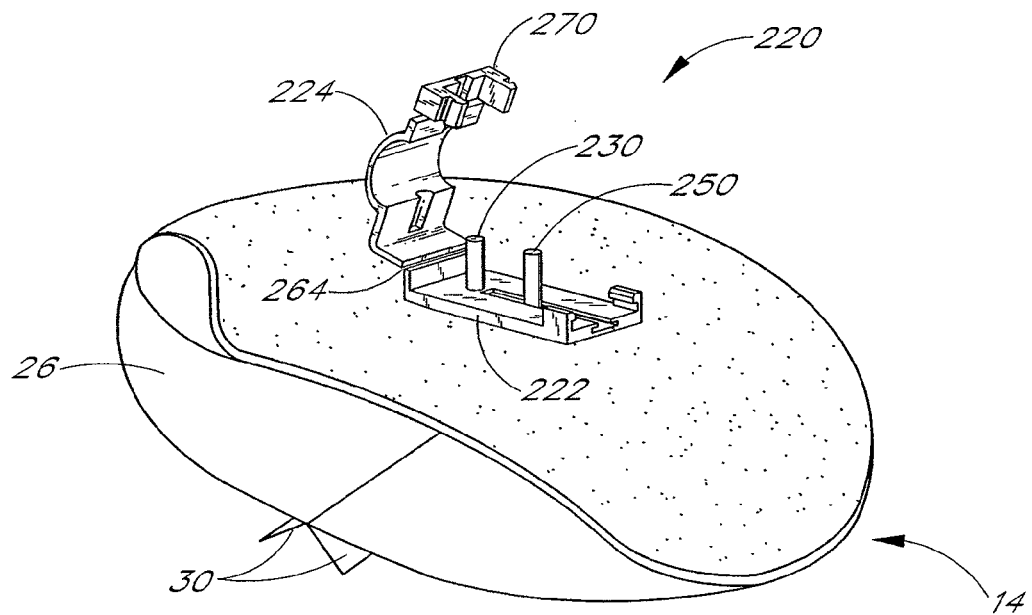
FIG. 20 is a perspective view of the anchoring system of FIG. 19 shown with the cover in an open position.
Figure 28:
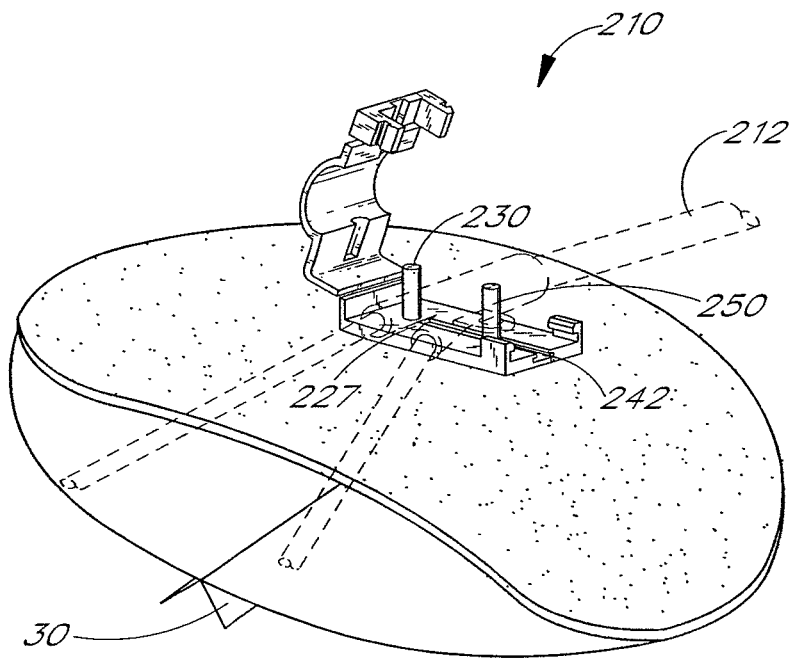
FIG. 28 is a perspective view of the anchoring system of FIG. 19 shown with the cover in a partially open position and with an exemplary catheter shown in phantom lines within the channel of the retainer.
Figure 29:
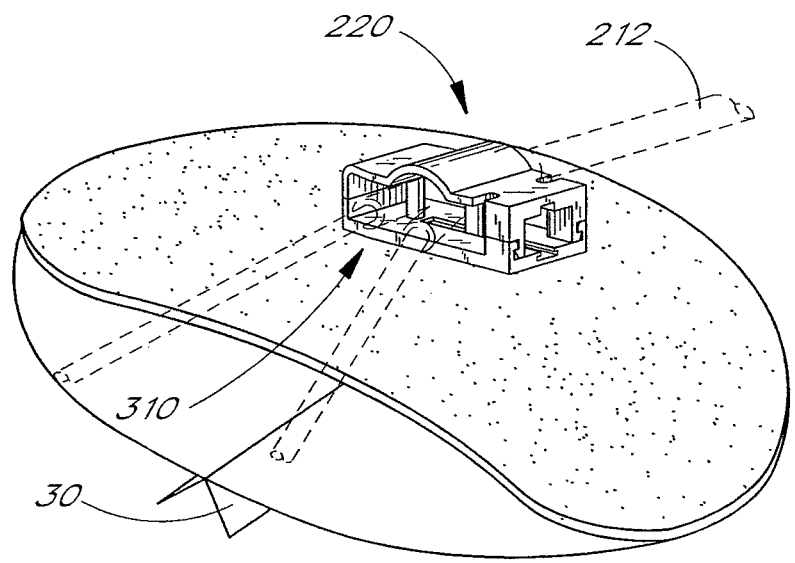
FIG. 29 is a perspective view of the anchoring system of FIG. 28 shown with the cover in a closed position.

An additional preferred embodiment of the present invention can be seen in FIGS. 19 and 20. The anchoring system 210 illustrated includes a retainer 220 and an anchor pad 294. The retainer 220 is sized and configured with one, and preferably two or more posts 230, 250 to accept and retain a section of a catheter 212 (FIG. 28) within the anchoring system 210, either directly or by way of a fitting 214. The retainer 220 comprises a base 222 and a cover 224. The cover 224 is detachably secured to the base 222 and movable between open and closed positions. The anchor pad 294 secures the retainer 220 to a patient's skin. The anchor pad 294 is substantially similar to the anchor pad described above for use in the previous embodiment of the invention.

Unlike the embodiments described above, this embodiment of the present invention does not make use of a post platform that comprises multiple posts. Rather, in the present embodiment, one post is integrally formed with the base of the retainer, and the other is inserted laterally into a track that runs along the bottom of the base. Because the same characteristics of flexibility and strength and ease of formation are present in this embodiment, the same materials are most preferable to construct the instant embodiment as were preferable to construct the prior embodiments.

Although the embodiment discussed below is described using particular ranges of sizes for various components, the sizes given are merely exemplary. Those skilled in the art will recognize that the components of any embodiment of the present invention described herein may be sized however is appropriate to the catheter or other device to be secured, or as is otherwise necessary according to the circumstances under which the device is used.

The illustrated embodiment shows the base 222 including first and second sides 226, 228. The first side 226 lies generally between one set of lateral ends of the base 222, and the second side 228 lies at an opposite set of lateral ends of the base 222.

Figure 21:
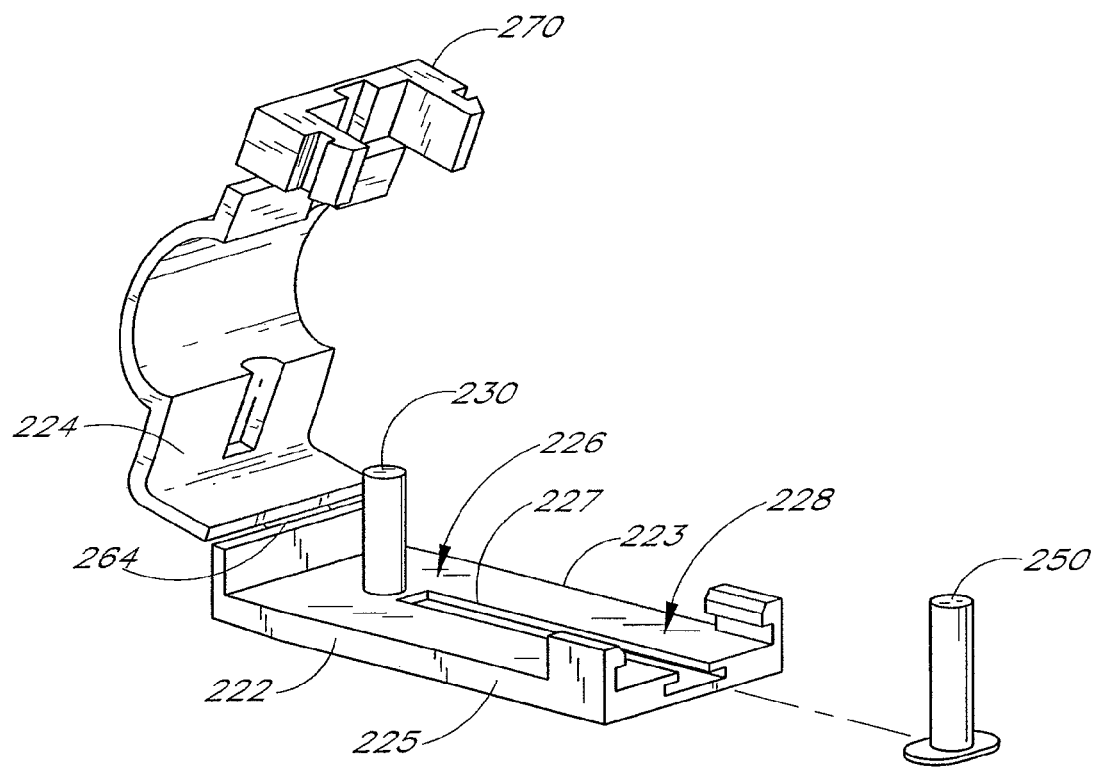
FIG. 21 is an exploded perspective view of the retainer of FIG. 19, illustrating the movable post detached from the retainer.

FIG. 21 shows a fixed post 230 that is integrally formed with and extends upwardly from the first side 226 of the base 222. The base 222 desirably includes a pair of posts (the second, movable post 250 is detailed below). The base 222, however, can include additional posts to suit a specific application. For example, where the retainer 220 is designed to secure a relatively large fitting, the base 222 can include four posts arranged at the corners of a rectangle, for greater stability. Similarly, three posts can be used to firmly anchor a Y-site fitting.

Figure 22:
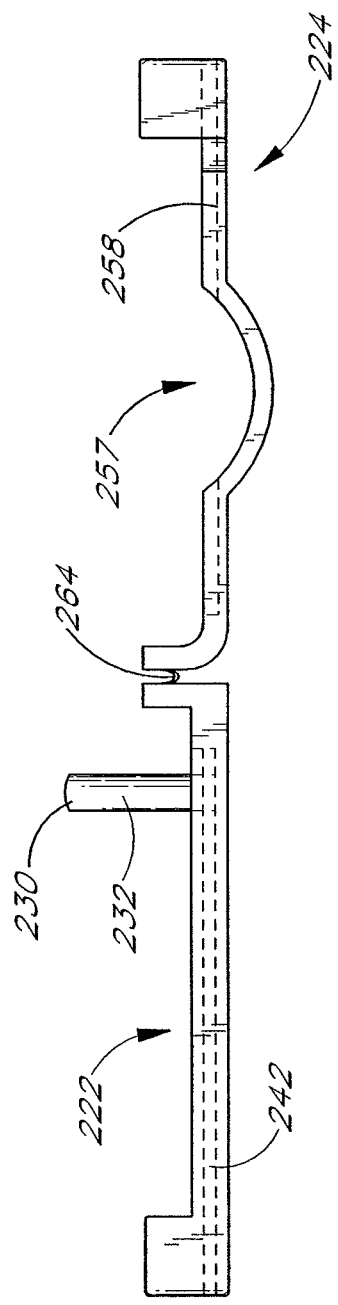
FIG. 22 is a front elevational view of the retainer of FIG. 19, with the cover shown in a fully open position.

As shown in FIG. 22, the fixed post 230 includes a shank or shaft 232, attached to and extending upwardly from the base 222. The post 230 can have a variety of lengths, depending upon the particular application and the particular fitting to which they interact to mount the catheter 212. For anchoring catheters and medical tubing, the fixed post 230 desirably has a length of about 20 mm or less, and more particularly a length of about 7 mm; however, longer or shorter lengths are also possible. The shaft 232 of the fixed post 230 has a diameter sufficient to perform its structural function, as described in more detail below, and depends on the material chosen for the base and post. The illustrated post 230 comprises a slightly elastic material, with a diameter between 0.5 mm and 3.0 mm and particularly about 1.5 mm. However, the illustrated embodiment shows the shaft 232 configured substantially as a cylinder to best match circular holes which are most commonly used on winged catheters or catheter fittings. However, the shaft can be configured with a host of other geometries, such as square, triangular, oval, polygon or the like, to match the hole configuration of various other catheters or catheter fittings.

Figure 23:
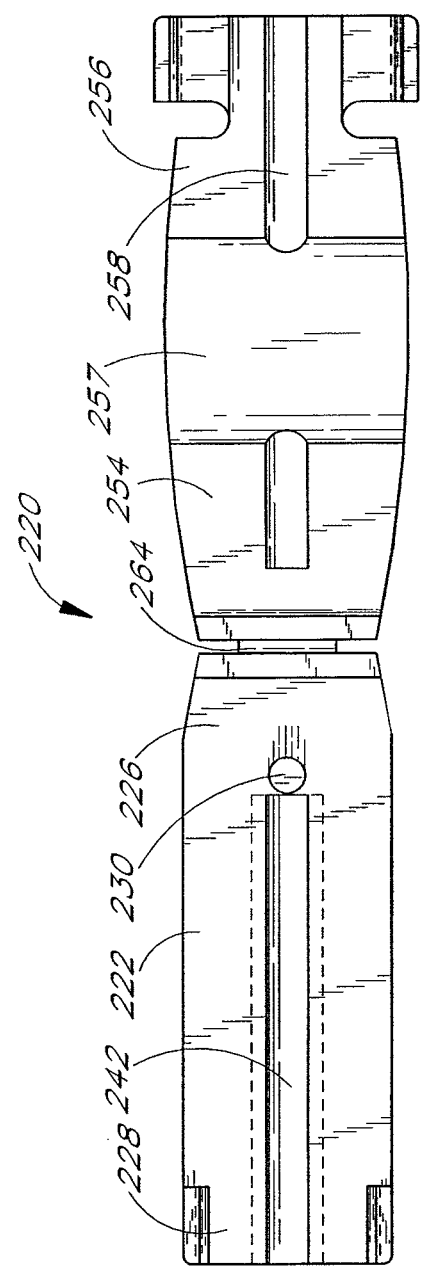
FIG. 23 is a top plan view of the retainer of FIG. 22, with the cover fully open.

FIG. 23 shows a track 242 formed in the base 222. The track 242 is arranged substantially linearly along the lateral axis and extends proximal the fixed post 230 to the second side 228 of the base 222. The track 242 has sufficient width to accommodate a movable element therein. The edges of the track 242 are of relatively smooth and solid construction such that the movable element can move or slide within the track 242 in a fluid manner without snagging on portions of the track 242.

Figure 24:
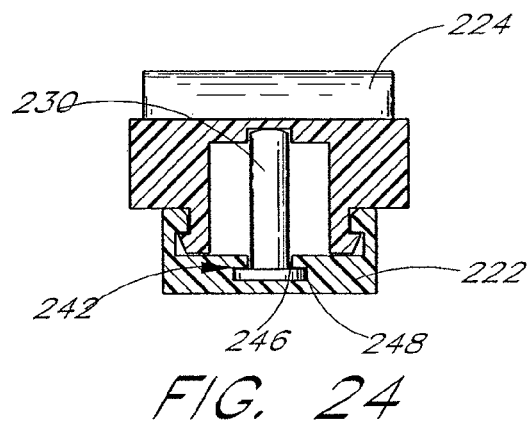
FIG. 24 is a cross-sectional view of the retainer taken along line 24-24 of FIG. 19 showing the movable post within a track of the retainer.

The track 242 has a substantially inverse T-shaped configuration, as can be seen in FIG. 24, with a first channel 246 and a second channel 248. The width of the second channel 248 is larger than the width of the first channel 246. A portion of the first channel 246 is desirably coplanar with the surface of the base 224 and extends toward the anchor pad 294. The first channel 246 desirably has a lateral width of 0.5 mm to 3.0 mm and particularly about 1.65 mm. The first channel 246 desirably has a transverse height of 0.1 mm to 0.8 mm and particularly about 0.64 mm and communicates with the second channel 248. The second channel 248 further extends toward the anchor pad 294. The width of the second channel 248 is desirably between about 0.5 mm and 8.0 mm and particularly about 3.0 mm. The second channel 248 desirably has a transverse height of 0.05 mm to 1.0 mm and particularly about 0.64 mm.

The T-shaped configuration of the track 242, achieved by the relationship between the first and second channels 246, 248, inhibits rocking of the movable element and retains it within the channels (detailed below). This configuration also provides for easy and inexpensive manufacture because a T-shaped track mold, desirably extruded by a T-shaped element, has an inherently stronger construction than other non I-beam structures, such as a dovetail shape. The track mold is thus less susceptible to damage from heat and pressure forces which occur during the molding process. In contrast, if a dovetail shape is used, the thinned edges become susceptible to melting and other deformations. Although a T-shaped track configuration is preferred, other track configurations, such as a dovetail shape, may be used with the anchoring system.

Figure 25:
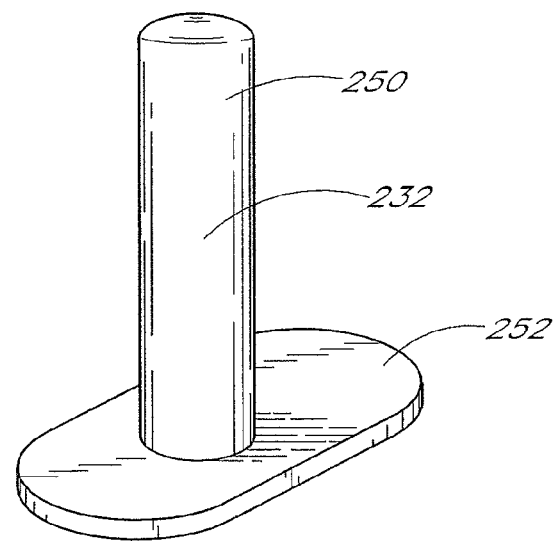
FIG. 25 is a perspective view of the movable post of FIG. 21.

FIG. 25 shows a movable post 250 including a shaft 232 sized and configured similar to the fixed post 230 and positioned along the base 222. The shaft 232 of the movable post 250 is sized and configured to be received into the first channel 246 of the track 242. The diameter of the shaft 232 is desirably similar to the lateral width of the first channel 246, but can have diameter that is appreciable greater or less than the lateral width of the first channel 246 depending on the particular application of the anchoring system and the materials used to form the various elements of the anchoring system. Desirably, the diameter of the shaft 232 may be made anywhere from about the same width to 1 mm less than the lateral width of the first channel 246, and particularly about 0.13 mm less. This close-fit configuration provides frictional forces between portions of the shaft 232 and first channel 242 and allows the post 250 to reluctantly slide within the first channel 246 of the track 242 while remaining substantially upstanding about the transverse axis.

The movable post 250 desirably further includes a platform 252 from which the post 250 extends. The platform 252 extends along a plane defined by the longitudinal and lateral axes and is sized and configured to be received into the second channel 248 of the track 242. Desirably, the relationship between the lateral width of the platform 252 and the lateral width of second channel 248 is similar to that of the movable post 250 and first channel 242 in order to similarly provide a close-fit configuration between the platform 252 and second channel 248. Thus, the platform 252 can reluctantly slide within the second channel 248 of the track 242 while remaining substantially upstanding about the transverse axis. Although the movable post shown in FIG. 25 has a platform whose length and width are different so as to form an elongated rounded rectangle, those of skill in the art will recognize that the platform may take on other shapes, such as square, oval, or circular without altering the operation of the post within the track.

By this post-platform design, the post 250 and platform 252 provides a substantially T-shaped structure that can be accommodated by the T-shaped track 242. Alternatively, if an alternative track configuration is used, such as dovetail shape, the post-platform design is modified to similarly provide a close-fit relationship with the track, as will be understood by one skilled in the art.

As detailed above, the substantially upstanding post 250 and platform 252, which are respectively closely fit into the smooth first and second channels 246, 248 of the track 242 cooperate to provide a movable structure which can reluctantly slide along the track 242 but which can remain upright, resist axial rocking, and prevent escape from the track 242 when axial or rotational forces are applied to the post 250. The reluctant sliding is such that a force applied by the finger(s) of a healthcare worker can slide the post 250 and platform 252 along the track 242. Any unintentional movement of the post 250 and platform 252, without such applied force, is resisted. The post 250 and platform 252 can also be reproducibly introduced into, and recalled from, the track 242 (FIG. 21). That is, the post and platform can enter the track 242 along the terminal portion of the track 242, which is co-extensive with the second side 228 of the base 222, and can similarly exit the track 242 from this terminal portion.

The platform 252 is desirably permanently affixed to the post 250 and formed unitarily therewith. However, the post 250 and platform 252 may be separately formed and then connected using any of a variety of suitable attachment means known to those skilled in the art. For example, the post can have a threaded portion that screws into a threaded portion of the platform, or the post can have a notch that is snapped into a recess in the platform. Chamfers can also be used to guide and position the post with respect to a seating area on the platform.

As best seen in FIGS. 22 and 23, the cover 224 has an elongate shape which desirably is coextensive with the planar size and shape of the base 222 (i.e., the cover desirably has the same geometric shape and size as the base 222); however, the cover 224 need not be the same size or shape as the base 222. For instance, the cover 224 can be sized to extend beyond any of the lateral, transverse, or longitudinal edges of the base 222 or, alternatively, can be sized so as to not extend to the lateral, transverse, or longitudinal edges of the base 222. The cover can also include a skirt or flange (not shown) that extends over and/or about the base 222 or any portion thereof.

The cover 224 desirably has a sufficient size to cover the posts 230, 250 in the base 222 and to accommodate a portion of the latch mechanism 270 and hinge 264 which operate between the base 222 and the cover 224 as described below. The cover 224 also desirably is of a dimension that provides for easy manipulation. For example, the cover's size easily accommodates the grasp of a healthcare worker, and allows for manipulation of the device while wearing surgical gloves.

The cover 224 includes a first side 254 which lies generally between one set of lateral ends of the cover 224. The first side 254 of the cover therefore generally corresponds to the first side 226 of the base 222. The cover 224 also has a second side 256. The second side 256 lies generally between one set of lateral ends of the cover 224, opposite of the first end, and therefore corresponds generally to the second side 228 of the base 222.

Still referring to FIGS. 22 and 23, a dome 257 is formed between the first side 254 and the second side 256 of the cover 224. The dome 257 provides a transversely extended area that can accommodate the central portion of larger, bulkier catheters and catheter fittings. Because many catheters and catheter fittings are manufactured "centrally bulky," the dome 257 allows these catheters or catheter fittings to be accepted into the retainer 220 when in the closed position and assists in the universal aspect of the present invention.

A recess 258 is formed as an elongated body on the cover 224 and runs generally parallel to the track 242 when the cover is in the closed position. The recess 258 is arranged to receive the distal ends of the posts 230, 250 when the cover 224 is in the closed position. The recess 258 allows the posts 230, 250 to avoid contact with or otherwise not impede the cover 224 when the cover 224 is moved to the closed position (the top of the posts 230, 250 may be at a transversely higher elevation than the bottom of the cover 224) and also inhibits motion of the posts in the longitudinal direction. The dome 257 may also serve as a partition to separate the recess 258 into first and second areas, each area being sized to accommodate a post.

The recess 258 desirably has a width slightly larger than the width of the first channel 246. This larger width compensates for inclination and "play" in the generally upstanding movable post 250, which may be angled anywhere between slightly greater or less than normal to the base 222 (generally 75 to 115 degrees). This play generally results from the close-fit configuration of the post 250 and platform 252, which are desirably configured dimensionally smaller than their corresponding tracks 246, 248. The transverse height of the recess 258 is desirably between about 1.0 mm and 2 mm and particularly about 1.27 mm. The recess 258 may have one or more chamfered edges (not shown) to transversely guide the post 230 into the recess 258.

Figure 26:
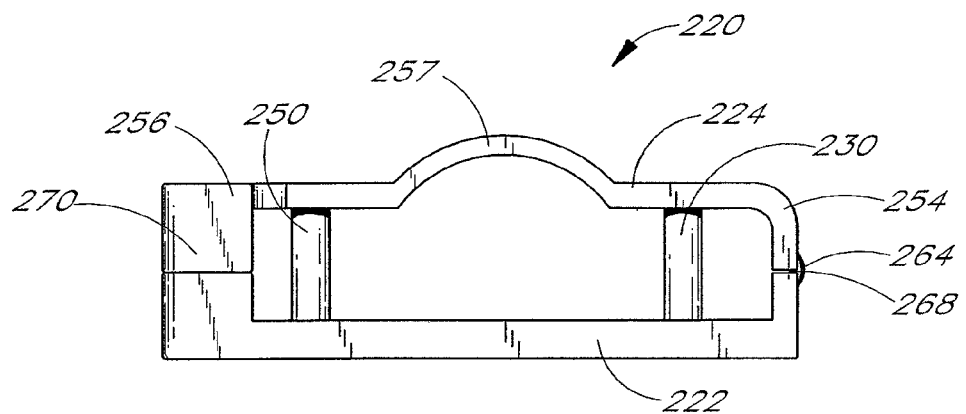
FIG. 26 is a front plan view of the assembled retainer of FIG. 19 with the cover shown in the closed position.
Figure 27:
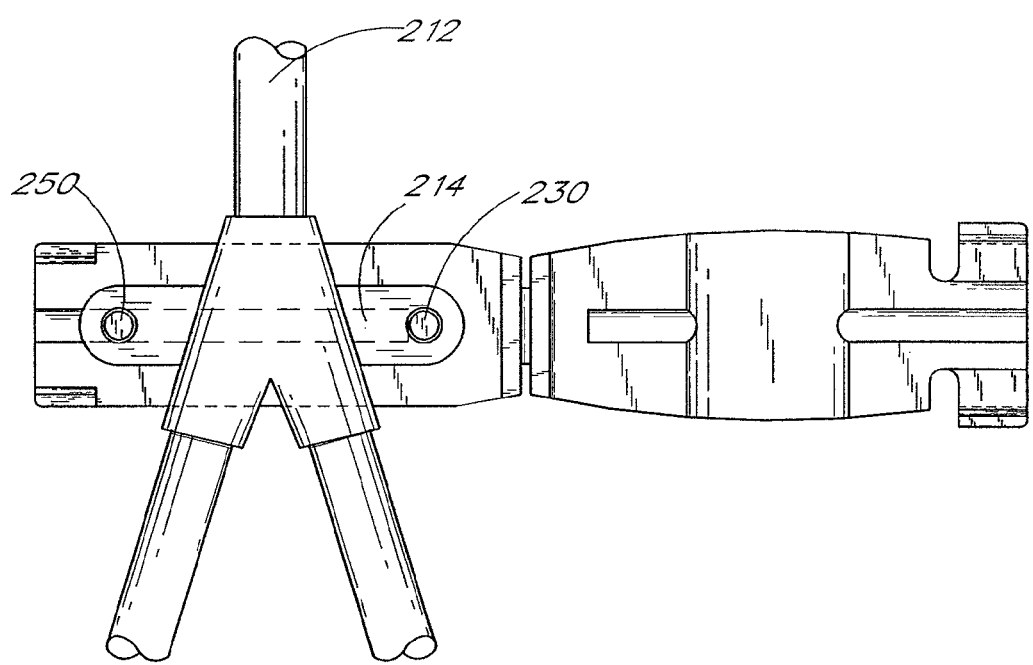
FIG. 27 is a top plan view of the retainer of FIG. 19 shown in the fully open position with an exemplary catheter shown inserted into the channel of the open retainer.

Although the recess 258 desirably forms an elongated body running generally parallel to the track 242 when the cover is in the closed position, a wide variety of other configurations may be used. For example, the first and second areas of the recess 258 can be modified so that the second area has a longer longitudinal length than the first area. So configured, the second area length can generally correspond to the track 242 length, while the first area length can generally correspond to the fixed post 230 diameter (FIG. 26). For another example, the recess may extend to the terminal ends of the first and second sides 254, 256 of the cover 224 for ease of manufacture. The only requirement of the recess 258 is the capability to receive the posts 230, 250 and allow the cover 224 to move to the fully closed position.

The flexible couplings that may be used to connect the cover 224 to the base 222 are substantially as described in the previous embodiments. The difference being that in the present embodiment the cover 224 comprises only a single piece and hence only a single hinge 264 is needed.

The means of operation is significantly the same for this anchoring system as for the previous system as well. The potential advantages are simplification of the manufacture and design.

Figure 30:
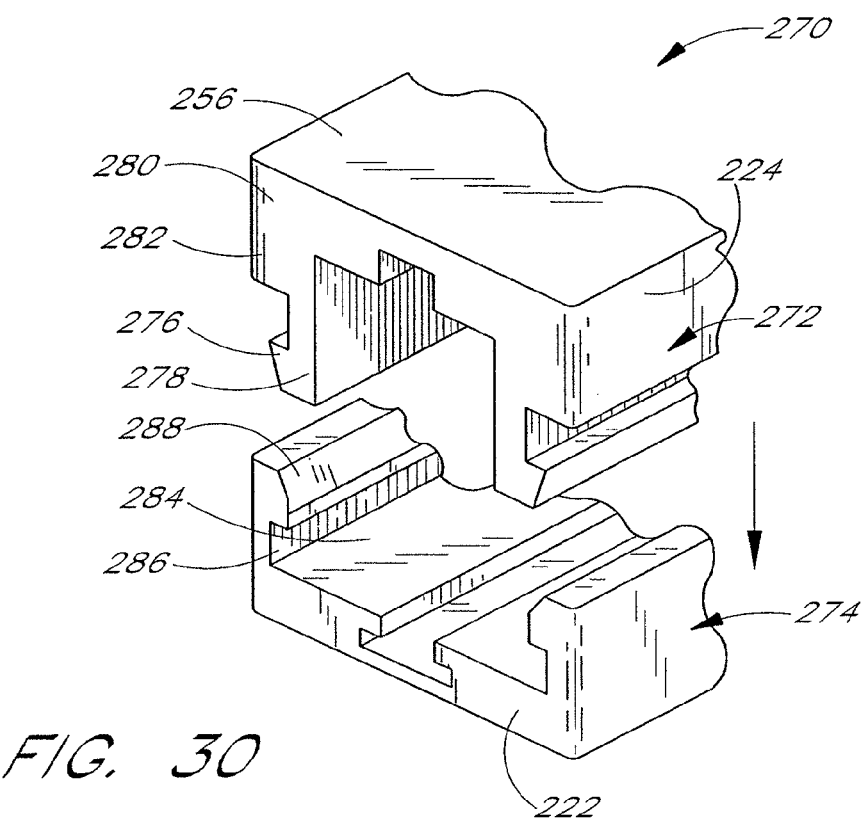
FIG. 30 is a partial, perspective view of the latching mechanism of the retainer of FIG. 19 shown in a partially open position.
Figure 31:
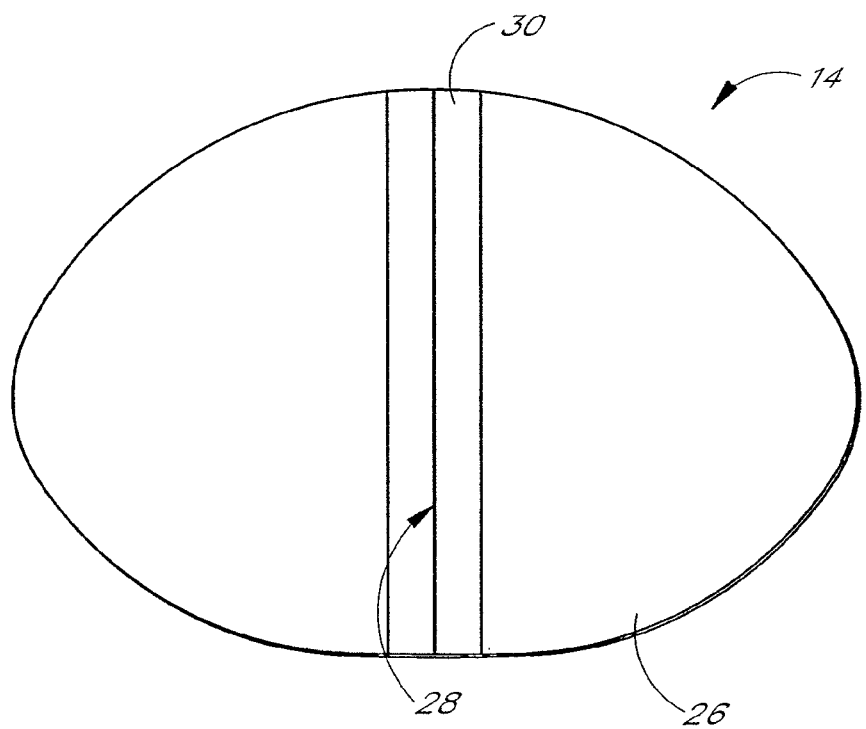
FIG. 31 is a bottom plan view of the anchor pad, showing a release liner.

The latching mechanism 270, while operating in a similar manner to the previously described embodiments, is slightly differently constructed in the present embodiment. As best seen in FIG. 30, each keeper 272 extends toward the base 222 from the second side 256 of the cover 224. A tang 276 is formed at a lower end 278 of the keeper 272. Desirably, the lower end 278 of the keeper 272 is relatively blunt and smooth to prevent it from puncturing the gloves or skin of a healthcare worker or catching on other materials. An operator lever 280 extends to the side of the keeper 272 and includes an enlarged platform or ear 282 at its outer end such that a component of a lateral force applied to the lever 280 will cause the keeper 272 to deflect inward. The entire keeper 272 desirably is formed with the cover 224 to form a unitary piece.

The latch mechanism 270 also includes a receptacle 284 that receives the tang 276 and at least a portion of the keeper 272. The latch receptacle 284 includes an inner notch 286 into which the tang 276 snaps into when the cover 224 is in the closed position; however, the tang 276 can be arranged in the receptacle 284 and the notch 286 be positioned on the keeper 272 to accomplish the same effect. The latch 274 desirably is formed with the base 222 as a unitary piece.

In the illustrated embodiment, the cover 224 includes two keepers 272 that are mirror images of each other. And, the latch 274 includes two notches 286, each of which is arranged to receive one of the keeper tangs 276 when the cover 224 is closed.

An entrance of the receptacle 284 includes chamfered edges 288. The chamfered edges 288 slope inward toward the center of the receptacle 284 to cause the keeper 272 to bend inward when inserted into the latch receptacle 284.

Lower Support Member

In some cases it may be advantageous to provide a lower support member which lies between the upper surface of the anchor pad and the bottom of the retainer base. The lower support member thereby provides a smooth surface for the bottom of the groove of the base, rather than having the bottom surface of the groove formed by the upper surface of the anchor pad. Additionally, because the lower support member now forms the bottom surface of the retainer, it is practical to adhere the entire bottom surface of the retainer to the anchor pad, even in embodiments making use of movable posts.

Figure 32:
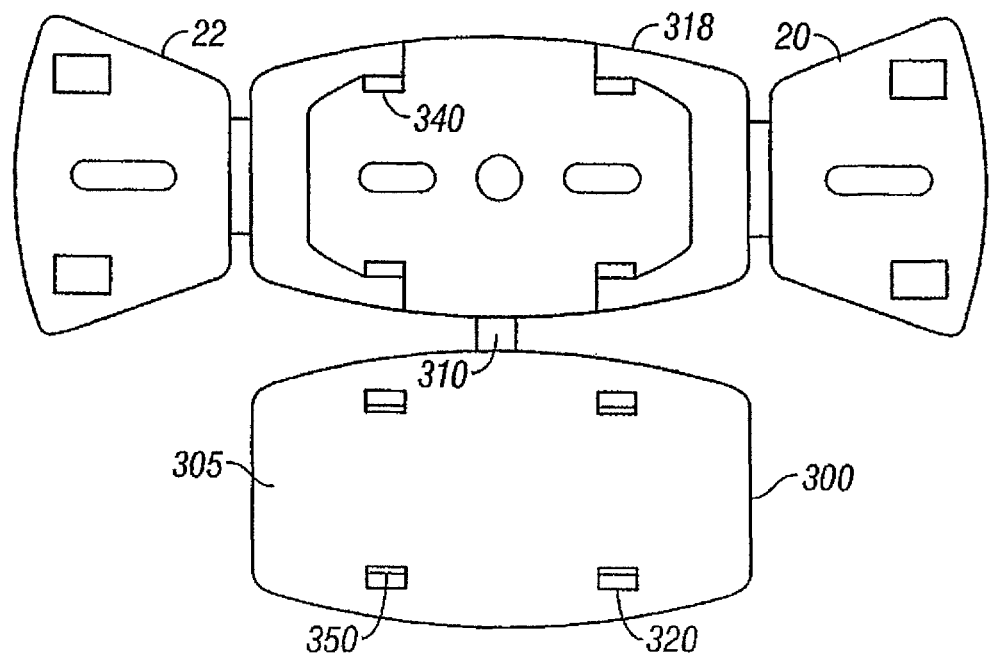
FIG. 32 is a top plan view of a unitary base and lower support member for an alternate retainer.
Figure 33:
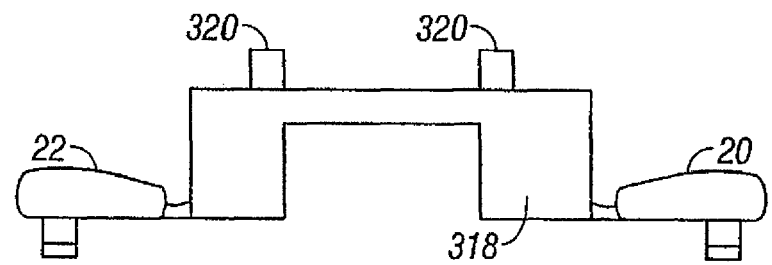
FIG. 33 is an inverted front elevational view of the unitary base and lower support member of FIG. 32.
Figure 34:
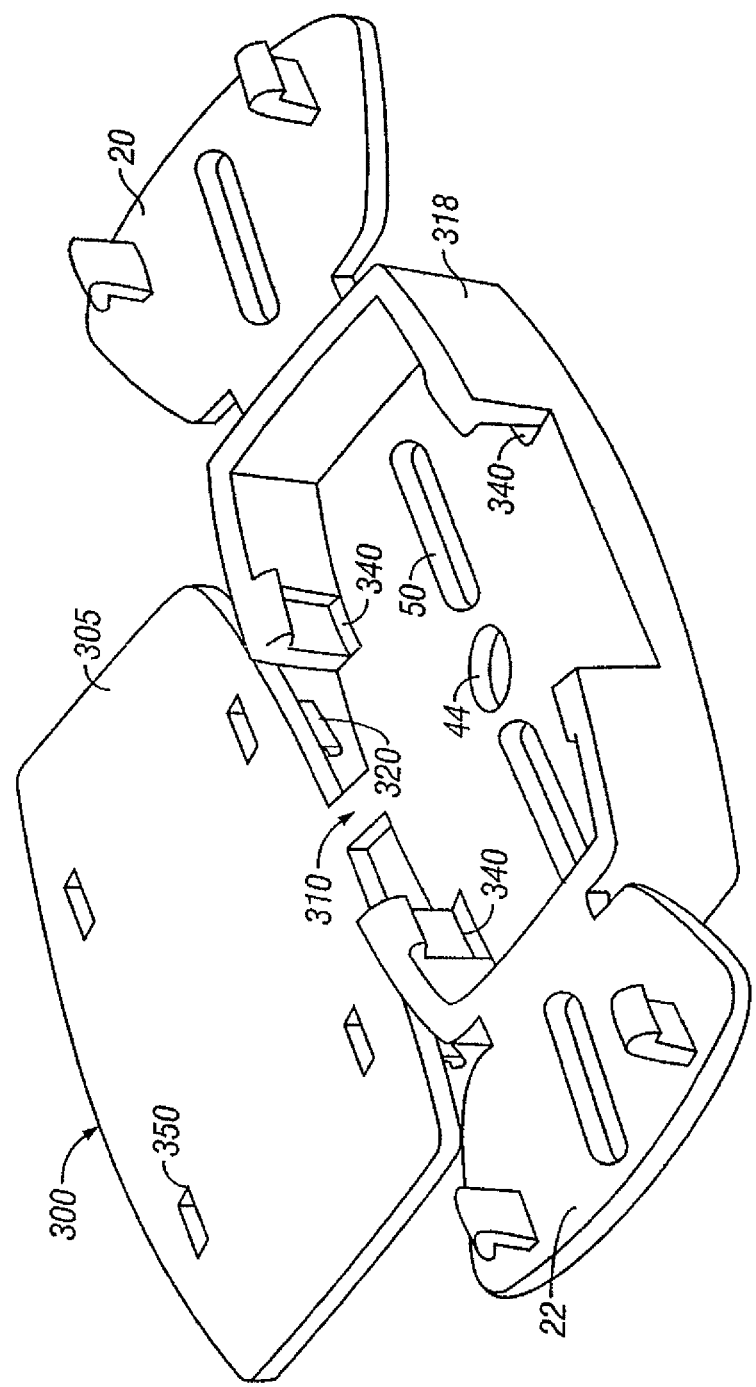
FIG. 34 is a perspective view of the unitary base and lower support member of FIG. 32.

The lower support member 300 as shown in FIGS. 32-34, comprises a generally flat plate 305 of generally the same planform shape as the lower portion of the retainer base 318. The lower support member 300 may preferably be manufactured from the same materials and using the same techniques as are suitable for the manufacture of the retainer base 318. In some preferred embodiments, the lower support member 300 and base 318 may be manufactured as a unitary piece, and then separated prior to assembly into the final retainer, as will be discussed below. Such a unitary lower support member 300 and base 318 are shown in FIGS. 32-34.

As can be seen in FIGS. 32-34, the lower support member 300 comprises a flat plate 305 and a set of tabs 320 which extend therefrom. In the illustrated embodiment, the tabs 320 extend in a direction opposite the direction in which the walls of the base 318 extend from the bottom of the base. However, the tabs 320 need not extend in this direction if the lower support member 300 is to be separated from the base 318 prior to assembly. Each tab 320 is preferably slightly flexible and contains a chamfered tang towards its tip. For manufacturing purposes it may be desirable to place a hole 350 on the plate 305 adjacent to each tab 320.

As also shown in FIGS. 32-34, the base 318 for use with the lower support member 300 preferably contains slots 340 in positions which correspond to the positions of the tabs 320 on the lower support member 300. As mentioned above, the base 318 and lower support member 300 may be manufactured as a single piece using injection molding or an other manufacturing process known in the art. When manufactured as a single piece, the lower support member 300 and base 318 are preferably connected by a thin leash of material 310, visible in FIGS. 32 and 34. This thin leash 310 may be broken or cut in order to separate the lower support member 300 from the base 318 prior to assembly. Desirably, the entire leash 310 is removed so that there is no stub of material projecting from the side of either the lower support member 300 or the base 318 of the retainer when it is in use upon a patient.

The base 318 as shown in FIGS. 32-34 also provides generally the same features as those discussed with respect to the base 18 shown in FIGS. 5-7 above. In particular, the base 318 provides a groove (not visible) on the underside of the base, as well as post openings. The post openings, as shown in FIG. 32, need not have a circular region, but rather only an elongated track 50. The elongated track 50 may contain a scalloped edge as described above in order to provide positions into which the posts may snap, or may have straight sides as shown in FIG. 32. It is also shown that the covers 20, 22 may be integrally molded with the base 318, as is described with respect to the base 18 in FIGS. 5-7 above.

After the base 318 and lower support member 300 are separated, an appropriate pair of posts 250 or a post platform may be inserted into position from the underside of the base 318. One post desirably extends through each of the elongated tracks 50 in the bottom of the base 318 when the platform or posts are inserted into the base 318. If a post platform with an attachment button is used, the attachment button is desirably inserted through the central circular opening 44 on the bottom of the base. The post platform may be as described above, or a pair of individual free standing posts 250 as shown in FIG. 25 may be used. In either case, it is desirable that the bottom of the platform of the posts lie within the groove of the base 318.

Once the post platform or posts 250 are in position, the lower support member 300 is pressed onto the bottom of the base 318 of the retainer and desirably secured in position. In the embodiment shown in FIGS. 32-34, the tabs 320 of the lower support member 300 will be inserted into the corresponding slots 340 in the bottom of the base. The chamfered tangs of the tabs 320 desirably cause each tab 320 to deflect as the tang passes through the slot 340, and then snap back toward its original position once the tang is beyond the slot 340 and within the interior space of the base 318. In this way, the interaction between the tabs 320 and the slot 340 and walls of the base 318 may secure the lower support member 300 upon the base 318.

The lower support member 300 may also be secured to the base 318 via adhesive. This may be used as an alternative to the use of tabs 320 and slots 340, or may be used in addition to the tabs 320 and slots 340 to provide improved securement between the lower support member 300 and the base 318. Desirably, when adhesive is used with any embodiment using posts which move, either as independent posts 250, or as in a post platform with connectors as shown in FIGS. 11A-11C, any adhesive used is preferably placed on a portion of the base 318 such that it does not interfere with the free motion of the posts within the groove of the base 318. Those of skill in the art will recognize that other means may also be used to attach the lower support member 300 to the bottom of the base 318. For instance, the lower support member 300 may be secured to the base 318 by ultrasonic welding.

Once assembled as described above, the retainer provides a pair of T-shaped tracks, similar to those described above with reference to FIG. 24, comprised of the groove of the base, and each post opening 50. The posts are free to move within these grooves as described above in order to accommodate medical articles of varying dimensions and configurations. The usage of the anchoring system formed using the lower support member 300 and base 318 shown in FIGS. 32-34 is substantially the same as that described with respect to FIGS. 5-7 above.

The various embodiments of anchoring systems and techniques described above in accordance with present invention thus provide a sterile, tight-gripping, needle- and tape-free way to anchor a medical article to a patient. The retainer thus eliminates use of tape, and if prior protocol required suturing, it also reduces the risk of accidental needle sticks, suture-wound-site infections and scarring. In addition, the techniques for the described retainers can be used with any of a wide variety of catheters, fittings, tubes, wires, and other medical articles. Patient comfort is also enhanced and application time is decreased with the use of the present anchoring system.

Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Furthermore, the skilled artisan will recognize the interchangeability of various features from different embodiments. For example, the scalloped edge of the elongated tracks may be adapted for use with the lower support member design shown in FIGS. 32-34. Similarly, the various bases, covers, posts, slots, hinges, anchor pads, post platforms, lower support members and latching mechanisms disclosed herein, as well as other known equivalents for each such feature, can be mixed and matched by one of ordinary skill in this art to construct anchoring systems in accordance with principles of the present invention.

Although this invention has been disclosed in the context of certain preferred embodiments and examples, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A retainer for securing a medical article to a patient, the medical article having two apertures, comprising:
   a pad having a lower surface, at least a portion of the lower surface being covered by an adhesive for attaching to the patient;
   a base supported by the pad and having a central opening;
   a post platform supported by the base;
   an attachment button disposed within the central opening, the attachment button limiting movement of the post platform in at least a transverse direction relative to the base;
   a first post extending from the base and being configured to fit within at least one of the two apertures in the medical article; and
   a second post extending from the post platform and being configured to fit within at least one of the two apertures in the medical article, the second post being movable relative to the first post so as to vary a distance between the first and second posts.

2. The retainer of claim 1, wherein the distance between the first and second posts varies along a lateral direction.

3. The retainer of claim 1, wherein the distance between the first and second posts varies along a longitudinal direction.

4. The retainer of claim 1, wherein the distance between the first and second posts varies along an axis that is skewed relative to a lateral direction.

5. The retainer of claim 1 further comprising at least one cover, the at least one cover being coupled to the base so as to move between an open position and a closed position.

6. The retainer of claim 5, wherein the at least one cover is disposed above at least a portion of the base when in the closed position.

7. The retainer of claim 5, wherein the at least one cover comprises a groove, at least a portion of one of the first and second posts being disposed in the groove when the at least one cover is in the closed position.

8. The retainer of claim 7, wherein the groove inhibits longitudinal movement of the post relative to the at least one cover when the at least one cover is in the closed position.

9. The retainer of claim 1, wherein the base is circular.

10. The retainer of claim 1, wherein the base is square.

11. The retainer of claim 1, wherein the base is trapezoidal.

12. A retainer for securing a medical article to a patient, the medical article having two apertures, comprising:
   a base;
   a first post platform supported by the base;
   a second post platform supported by the base;
   a first post extending from the first post platform and being configured to fit within at least one of the two apertures in the medical article; and
   a second post extending from the second post platform and being configured to fit within at least one of the two apertures in the medical article, the second post platform being movable relative to the first post platform so as to vary a distance between the first and second posts.

13. The retainer of claim 12 further comprising an attachment button, the attachment button limiting movement of at least one of the first and second post platforms in at least a transverse direction relative to the base.

14. The retainer of claim 13 further comprising a pad having a lower surface and supporting the base, at least a portion of the lower surface being covered by an adhesive for attaching to the patient.

15. A retainer for securing a medical article having at least two apertures to the body of a patient, comprising:
   a base defining a plane;
   a platform supported by the base;
   a first post extending from the base; and
   a second post extending from the platform, the platform being movable in a direction parallel to the plane between a first position and a second position so as to vary a distance between the first and second posts.

16. The retainer of claim 15 further comprising a pad having a lower surface and supporting the base, at least a portion of the lower surface being covered by an adhesive for attaching to the patient.

17. The retainer of claim 15 further comprising at least one cover, the at least one cover being coupled to the base so as to move between an open position and a closed position.

18. The retainer of claim 15, wherein the distance between the first and second posts when in the first position is greater when measured in at least a lateral direction than when in the second position.

19. The retainer of claim 15, wherein the distance between the first and second posts when in the first position is greater when measured in at least a longitudinal direction than when in the second position.

20. A retainer for securing a medical article having at least two apertures to the body of a patient, comprising:
   a base;
   at least one post platform slidingly disposed on the base; and
   two posts, at least one of the two posts being disposed on the at least one post platform so as to move relative to the other post, the two posts being spaced apart so as to be received within the at least two apertures in the medical article.

* * * * *